(12) United States Patent
Lee et al.

(10) Patent No.: US 11,504,388 B2
(45) Date of Patent: Nov. 22, 2022

(54) TRANS-SPLICING RIBOZYME TARGETING RHODOPSIN TRANSCRIPT AND USES THEREOF

(71) Applicant: Rznomics Inc., Yongin-si (KR)

(72) Inventors: Seong-Wook Lee, Seoul (KR); Ji Hyun Kim, Seoul (KR); Seung Ryul Han, Yongin-si (KR)

(73) Assignee: Rznomics Inc., Yongin-si (KR)

( * ) Notice: Subject to any disclaimer, the term of this patent is extended or adjusted under 35 U.S.C. 154(b) by 0 days.

(21) Appl. No.: 17/646,244

(22) Filed: Dec. 28, 2021

(65) Prior Publication Data

US 2022/0117996 A1 Apr. 21, 2022

Related U.S. Application Data

(63) Continuation-in-part of application No. PCT/KR2021/009555, filed on Jul. 23, 2021.

(30) Foreign Application Priority Data

Jul. 24, 2020 (KR) .................. 10-2020-0092265
Jul. 23, 2021 (KR) .................. 10-2021-0096986

(51) Int. Cl.
| | | |
|---|---|---|
| *C07H 21/04* | (2006.01) | |
| *A61K 31/7088* | (2006.01) | |
| *A61P 27/02* | (2006.01) | |
| *A61K 35/761* | (2015.01) | |
| *C12N 15/113* | (2010.01) | |
| *C12N 15/86* | (2006.01) | |

(52) U.S. Cl.
CPC ........ *A61K 31/7088* (2013.01); *A61K 35/761* (2013.01); *A61P 27/02* (2018.01); *C12N 15/113* (2013.01); *C12N 15/86* (2013.01); *C12N 2310/11* (2013.01); *C12N 2310/12* (2013.01); *C12N 2750/14143* (2013.01)

(58) Field of Classification Search
None
See application file for complete search history.

(56) References Cited

U.S. PATENT DOCUMENTS

2003/0069195 A1 4/2003 Farrar et al.
2021/0207147 A1* 7/2021 Lewin .................. C12N 15/86

FOREIGN PATENT DOCUMENTS

KR 10-2010-0024055 A 3/2010
KR 10-2010-0052070 A 5/2010

OTHER PUBLICATIONS

Fiskaa et al. ("RNA reprogramming and repair based on trans-splicing group I ribozymes." New biotechnology 27.3 (2010): 194-203).*
Lewin et al. ("Ribozyme gene therapy: applications for molecular medicine." Trends in molecular medicine 7.5 (2001): 221-228).*
Trapani et al. ("Vector platforms for gene therapy of inherited retinopathies." Progress in retinal and eye research 43 (2014): 108-128).*
Translation of Written Opinion of the International Searching Authority, for PCT/KR2021/009555, dated Nov. 9, 2021.
International Search Report for PCT/KR2021/009555, dated Nov. 9, 2021 (in English).
Office Action dated Oct. 29, 2021 in Korean Application No. 10-2021-0096986.
Office Action dated Jan. 27, 2022 in Korean Application No. 10-2021-0096986.
Notice of Allowance dated Apr. 7, 2022 issued by the Korean Patent Office in Korean Application No. 10-2021-0096986.
NCBI Reference Sequence: NM_000539.3 Homo sapiens rhodopsin (RHO), mRNA, Jan. 30, 2022 (6 pages total).
Adeline Berger et al., "Repair of Rhodopsin mRNA by Spliceosome-Mediated RNA Trans-Splicing: A New Approach for Autosomal Dominant Retinitis Pigmentosa", The American Society of Gene & Cell Therapy, May 2015, pp. 918-930, vol. 23, No. 5.
Uwe Kohler et al., "Trans-splicing Ribozymes for Targeted Gene Delivery", J. Mol. Biol., 1999, pp. 1935-1950, 285.
Dibyendu Chakraborty et al., "In vitro Analysis of Ribozyme-mediated Knockdown of an ADRP", Adv Exp Med Biol., 2008, pp. 97-106, 613.
Dimitra Athanasiou et al., "The molecular and cellular basis of rhodopsin retinitis pigmentosa reveals potential strategies for therapy", Prog Retin Eye Res., Jan. 2018, pp. 1-23, 62.
Notification of Transmittal of the International Search Report and the Written Opinion of the International Searching Authority, or the Declaration for PCT/KR2021/009555, dated Nov. 9, 2021 PCT/ISA/220].
Written Opinion for PCT/KR2021/009555, dated Nov. 9, 2021 [PCT/ISA/237].

* cited by examiner

Primary Examiner — Kimberly Chong
(74) Attorney, Agent, or Firm — Sughrue Mion, PLLC

(57) ABSTRACT

A trans-splicing ribozyme capable of splicing a rhodopsin transcript at a target splicing site and containing a sequence that is capable of complementarily binding to a target binding site of the rhodopsin transcript is disclosed. The trans-splicing ribozyme may further containing a desired rhodopsin transcript at 3'-end. The trans-splicing ribozyme may further contains an antisense sequence that is complementary to a region downstream the target binding site of the rhodopsin transcript. A nucleotide molecule encoding the trans-splicing ribozyme is also disclosed. Delivery systems to delivery the nucleotide molecule and/or the trans-splicing ribozyme to target tissue or cells as well as uses of the trans-splicing ribozyme, the nucleotide molecule, delivery systems, or pharmaceutical compositions containing any of them are also disclosed.

22 Claims, 31 Drawing Sheets
(5 of 31 Drawing Sheet(s) Filed in Color)
Specification includes a Sequence Listing.

FIG. 3B

| Reaction site (nt) | In vitro mapping | | In vivo mapping | |
| --- | --- | --- | --- | --- |
| | Number of clone (WT RHO) | Number of clone (MT RHO) | Number of clone (WT RHO) | Number of clone (MT RHO) |
| +30 | - | - | 2 | 2 |
| +35 | - | - | 1 | - |
| +42 | - | - | - | 1 |
| +43 | - | - | - | 1 |
| +52 | - | - | 1 | - |
| +54 | - | - | 1 | 3 |
| +55 | 4 | 15 | 1 | 1 |
| +59 | 23 | 20 | 1 | 4 |
| +75 | 2 | 1 | 1 | 1 |
| +96 | AUG initiation codon | | | |
| +97 | - | - | - | 1 |
| +116 | 1 | 1 | 1 | - |
| +121 | - | - | 2 | 2 |
| +123 | 1 | 3 | 6 | 1 |
| +127 | - | - | 1 | - |
| +132 | - | - | 1 | - |
| +140 | - | - | 1 | 2 |
| +154 | 1 | - | - | - |
| +165 | - | - | 2 | 1 |
| +171 | - | 1 | - | - |
| +187 | - | - | - | 1 |
| +191 | - | - | 1 | 1 |
| +207 | - | 1 | - | - |
| +215 | - | - | - | 1 |
| +222 | - | - | 2 | - |
| +230 | - | 1 | - | - |
| +232 | 4 | 3 | - | - |
| +235 | 1 | - | - | - |
| +244 | 1 | - | - | - |
| +256 | 3 | 8 | - | 2 |
| +262 | - | - | - | 1 |
| +273 | 4 | 4 | 2 | 2 |
| +298 | 1 | - | 1 | - |
| +308 | - | - | 1 | - |
| +381 | 1 | 2 | - | - |
| +403 | 1 | - | - | - |
| +681 | 1 | 1 | - | - |
| +688 | - | - | - | 1 |

FIG. 6A
1st design vs 2nd design
RHO wild substrate transfection
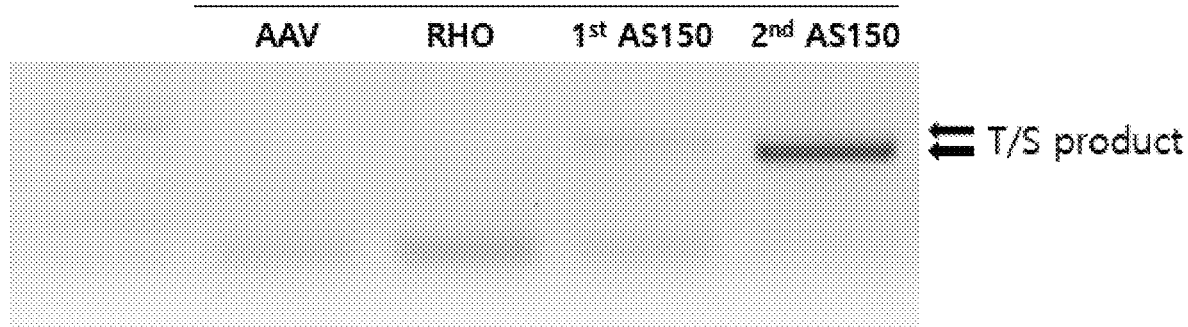
RHO P23H substrate transfection
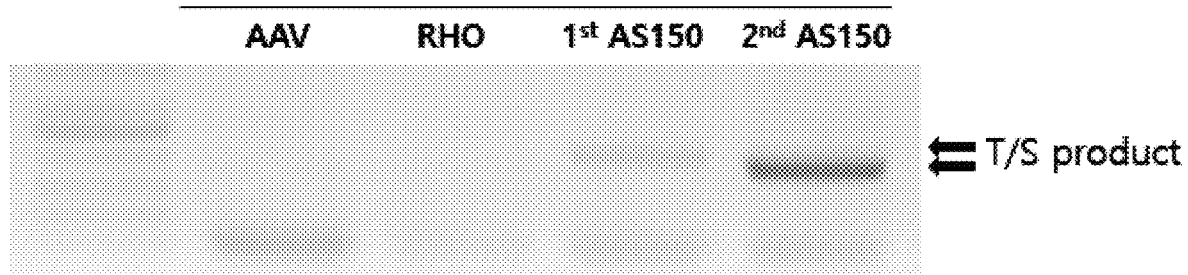

FIG. 6B
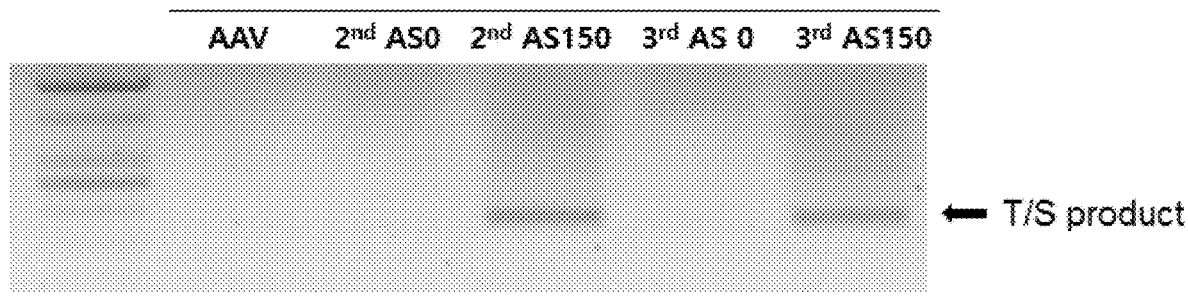
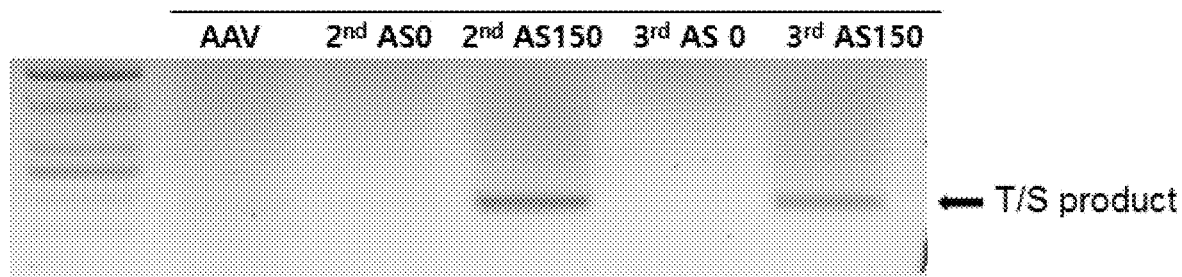

FIG. 6C
2nd design ribozyme optimization
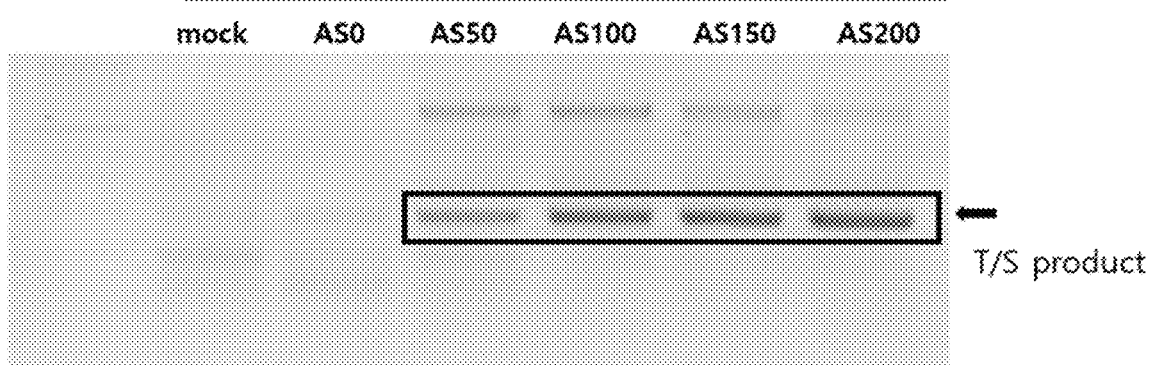
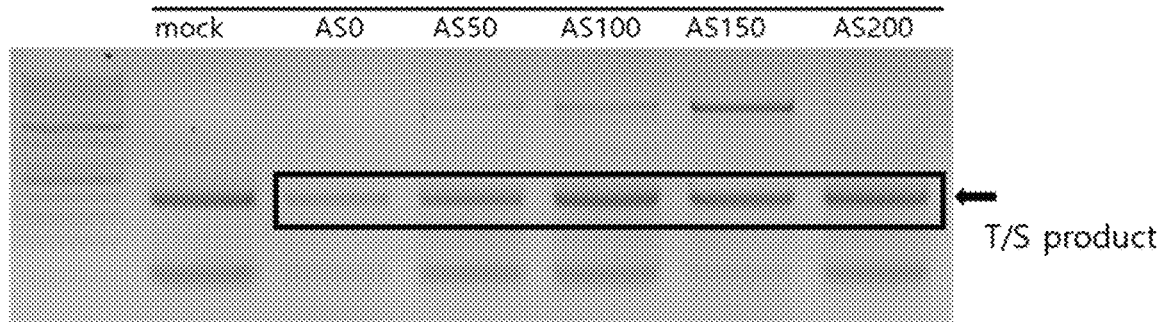

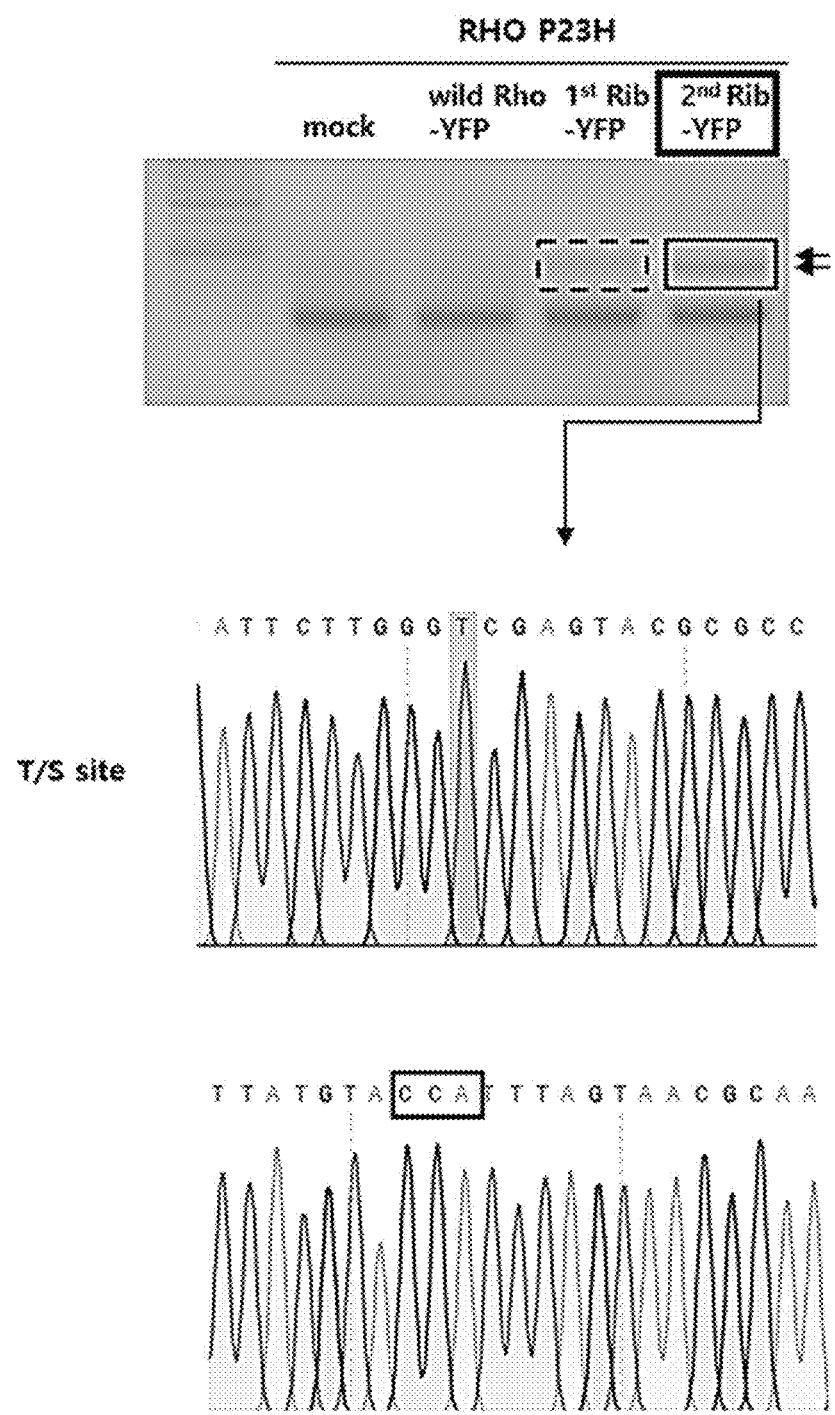

FIG. 7B
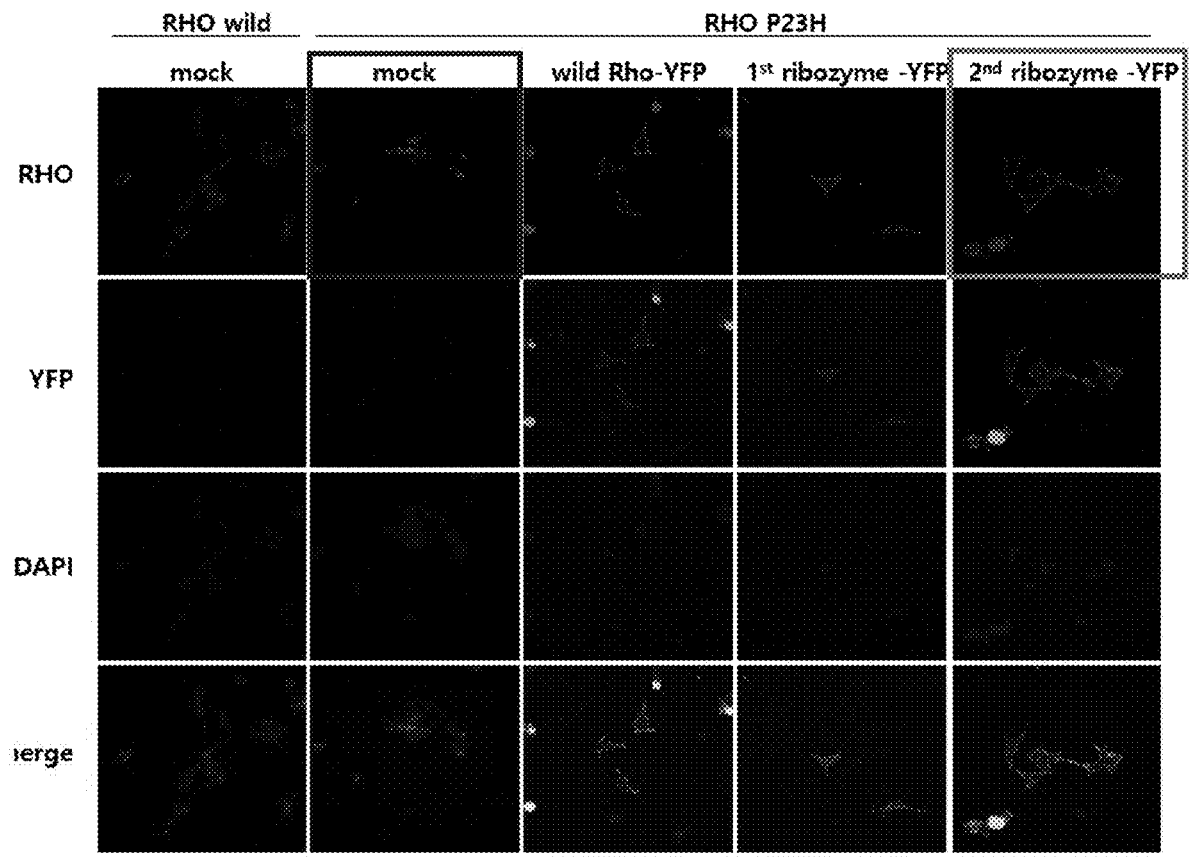
P23H mutant RHO stable cell
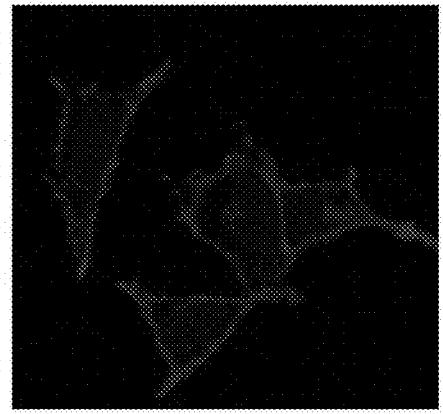
2nd ribozyme-YFP

SEQUENCE LISTING

<160> NUMBER OF SEQ ID NOS: 21

<210> SEQ ID NO 1
<211> LENGTH: 2768
<212> TYPE: DNA
<213> ORGANISM: Homo sapiens

<400> SEQUENCE: 1

```
agagtcatcc agctggagcc ctgagtggct gagctcaggc cttcgcagca ttcttgggtg      60
ggagcagcca cgggtcagcc acaagggcca cagccatgaa tggcacagaa ggccctaact     120
tctacgtgcc cttctccaat gcgacgggtg tggtacgcag ccccttcgag tacccacagt     180
actacctggc tgagccatgg cagttctcca tgctggccgc ctacatgttt ctgctgatcg     240
tgctgggctt ccccatcaac ttcctcacgc tctacgtcac cgtccagcac aagaagctgc     300
gcacgcctct caactacatc ctgctcaacc tagccgtggc tgacctcttc atggtcctag     360
gtggcttcac cagcaccctc tacacctctc tgcatggata cttcgtcttc gggcccacag     420
gatgcaattt ggagggcttc tttgccaccc tgggcggtga aattgccctg tggtccttgg     480
tggtcctggc catcgagcgg tacgtggtgg tgtgtaagcc catgagcaac ttccgcttcg     540
gggagaacca tgccatcatg ggcgttgcct tcacctgggt catggcgctg gcctgcgccg     600 caccccact cgccggctgg tccaggtaca tccccgaggg cctgcagtgc tcgtgtggaa     660
tcgactacta cacgctcaag ccggaggtca acaacgagtc ttttgtcatc tacatgttcg     720
tggtccactt caccatcccc atgattatca tcttttttctg ctatgggcag ctcgtcttca     780
ccgtcaagga ggccgctgcc cagcagcagg agtcagccac cacacagaag gcagagaagg     840
aggtcacccg catggtcatc atcatggtca tcgctttcct gatctgctgg gtgccctacg     900
ccagcgtggc attctacatc ttcacccacc agggctccaa cttcggtccc atcttcatga     960
ccatcccagc gttctttgcc aagagcgccg ccatctacaa ccctgtcatc tatatcatga    1020
tgaacaagca gttccggaac tgcatgctca ccaccatctg ctgcggcaag aacccactgg    1080
gtgacgatga ggcctctgct accgtgtcca agacggagac gagccaggtg gccccggcct    1140
aagacctgcc taggactctg tggccgacta taggcgtctc ccatccccta caccttcccc    1200
cagccacagc catcccacca ggagcagcgc ctgtgcagaa tgaacgaagt cacataggct    1260
```

```
ccttaattttt ttttttttttt ttaagaaata attaatgagg ctcctcactc acctgggaca    1320
gcctgagaag ggacatccac caagacctac tgatctggag tcccacgttc cccaaggcca    1380
gcgggatgtg tgcccctcct cctcccaact catctttcag gaacacgagg attcttgctt    1440
tctggaaaag tgtcccagct tagggataag tgtctagcac agaatggggc acacagtagg    1500
tgcttaataa atgctggatg gatgcaggaa ggaatggagg aatgaatggg aagggagaac    1560
atatctatcc tctcagaccc tcgcagcagc agcaactcat acttggctaa tgatatggag    1620
cagttgtttt tccctccctg ggcctcactt tcttctccta taaaatggaa atcccagatc    1680
cctggtcctg ccgacacgca gctactgaga agaccaaaag aggtgtgtgt gtgtctatgt    1740
gtgtgtttca gcactttgta aatagcaaga agctgtacag attctagtta atgttgtgaa    1800
taacatcaat taatgtaact agttaattac tatgattatc acctcctgat agtgaacatt    1860
ttgagattgg gcattcagat gatggggttt cacccaacct tggggcaggt ttttaaaaat    1920
tagctaggca tcaaggccag accagggctg ggggttgggc tgtaggcagg gacagtcaca    1980
ggaatgcaga atgcagtcat cagacctgaa aaaacaacac tggggagggg ggacggtgaa    2040
ggccaagttc ccaatgaggg tgagattggg cctggggtct caccctagt gtggggcccc    2100 aggtcccgtg cctccccttc ccaatgtggc ctatggagag acaggccttt ctctcagcct    2160
ctggaagcca cctgctcttt tgctctagca cctgggtccc agcatctaga gcatggagcc    2220
tctagaagcc atgctcaccc gcccacattt aattaacagc tgagtccctg atgtcatcct    2280
tatctcgaag agcttagaaa caaagagtgg gaaattccac tgggcctacc ttccttgggg    2340
atgttcatgg gccccagttt ccagtttccc ttgccagaca agcccatctt cagcagttgc    2400
tagtccattc tccattctgg agaatctgct ccaaaaagct ggccacatct ctgaggtgtc    2460
agaattaagc tgcctcagta actgctcccc cttctcccata taagcaaagc cagaagctct    2520
agctttaccc agctctgcct ggagactaag gcaaattggg ccattaaaag ctcagctcct    2580
atgttggtat taacggtggt gggttttgtt gctttcacac tctatccaca ggatagattg    2640
aaactgccag cttccaccctg atccctgacc ctgggatggc tggattgagc aatgagcaga    2700
gccaagcagc acagagtccc ctggggctag aggtggagga ggcagtcctg ggaatgggaa    2760
aaaccccca                                                           2768

<210> SEQ ID NO 2
<211> LENGTH: 405
<212> TYPE: DNA
<213> ORGANISM: Artificial Sequence
<220> FEATURE:
<223> OTHER INFORMATION: Sequence encoding trans-splicing ribozyme

<400> SEQUENCE: 2
gctcccgccc aaaaaagtta tcaggcatgc acctggtagc tagtctttaa accaatagat     60
tgcatcggtt taaaggcaa gaccgtcaaa ttgcgggaaa ggggtcaaca gccgttcagt    120
accaagtctc agggaaact ttgagatggc cttgcaaagg gtatggtaat aagctgacgg    180
acatggtcct aaccacgcag ccaagtccta agtcaacaga tcttctgttg atatggatgc    240
agttcacaga ctaaatgtcg gtcgggaag atgtattctt ctcataagat atagtcggac    300
ctctccttaa tgggagctag cggatgaagt gatgcaacac tggagccgct gggaactaat    360
ttgtatgcga aagtatattg attagttttg gagtactcgg ggagc                   405

<210> SEQ ID NO 3
<211> LENGTH: 409
```

<212> TYPE: DNA
<213> ORGANISM: Artificial Sequence
<220> FEATURE:
<223> OTHER INFORMATION: Sequence encoding trans-splicing ribozyme

<400> SEQUENCE: 3

```
cgtactccgc ccaaaaaagt tatcaggcat gcacctggta gctagtcttt aaaccaatag      60
attgcatcgg tttaaaaggc aagaccgtca aattgcggga aaggggtcaa cagccgttca     120
gtaccaagtc tcaggggaaa ctttgagatg gccttgcaaa gggtatggta ataagctgac     180
ggacatggtc ctaaccacgc agccaagtcc taagtcaaca gatcttctgt tgatatggat     240
gcagttcaca gactaaatgt cggtcgggga agatgtattc ttctcataag atatagtcgg     300
acctctcctt aatgggagct agcggatgaa gtgatgcaac actggagccg ctgggaacta     360
atttgtatgc gaaagtatat tgattagttt tggagtactc gcgagtacg                 409
```

<210> SEQ ID NO 4
<211> LENGTH: 409
<212> TYPE: DNA
<213> ORGANISM: Artificial Sequence
<220> FEATURE:
<223> OTHER INFORMATION: Sequence encoding trans-splicing ribozyme

<400> SEQUENCE: 4

```
cgtactccgc ccaaaaaagt tatcaggcat gcacctggta gctagtcttt aaaccaatag      60
attgcatcgg tttaaaaggc aagaccgtca aattgcggga aaggggtcaa cagccgttca     120
gtaccaagtc tcaggggaaa ctttgagatg gccttgcaaa gggtatggta ataagctgac     180
ggacatggtc ctaaccacgc agccaagtcc taagtcaaca gatcttctgt tgatatggat     240
gcagttcaca gactaaatgt cggtcgggga agatgtattc ttctcataag atatagtcgg     300
acctctcctt aatgggagct agcggatgaa gtgatgcaac actggagccg ctgggaacta     360
atttgtatgc gaaagtatat tgattagttt tggagtactc gccagtacg                 409
```

<210> SEQ ID NO 5
<211> LENGTH: 387
<212> TYPE: DNA
<213> ORGANISM: Artificial Sequence
<220> FEATURE:
<223> OTHER INFORMATION: Sequence encoding Ribozyme* (trans-splicing
      ribozyme without IGS sequence)

<400> SEQUENCE: 5

```
aaaagttatc aggcatgcac ctggtagcta gtctttaaac caatagattg catcggttta      60
aaaggcaaga ccgtcaaatt gcgggaaagg ggtcaacagc cgttcagtac caagtctcag     120
gggaaacttt gagatggcct tgcaaagggt atggtaataa gctgacggac atggtcctaa     180
ccacgcagcc aagtcctaag tcaacagatc ttctgttgat atggatgcag ttcacagact     240
aaatgtcggt cggggaagat gtattcttct cataagatat agtcggacct ctccttaatg     300
ggagctagcg gatgaagtga tgcaacactg gagccgctgg gaactaattt gtatgcgaaa     360
gtatattgat tagttttgga gtactcg                                         387
```

<210> SEQ ID NO 6
<211> LENGTH: 150
<212> TYPE: DNA
<213> ORGANISM: Artificial Sequence
<220> FEATURE:
<223> OTHER INFORMATION: Sequence encoding AS150

-continued

<400> SEQUENCE: 6

```
ggcggccagc atggagaact gccatggctc agccaggtag tactgtgggt actcgaagtg      60
gctgcgtacc acacccgtcg cattggagaa gggcacgtag aagttagggc cttctgtgcc     120
attcatggct gtggcccttg tggctgaccc                                      150
```

<210> SEQ ID NO 7
<211> LENGTH: 400
<212> TYPE: DNA
<213> ORGANISM: Artificial Sequence
<220> FEATURE:
<223> OTHER INFORMATION: Sequence encoding SD/SA

<400> SEQUENCE: 7

```
aaaaaatgct tcttcttttt aatatacttt tttgtttatc ttatttctaa tactttccct      60
aatctctttc tttcagggca ataatgatac aatgtatcat gcctctttgc accattctaa    120
agaataacag tgataatttc tgggttaagg caatagcaat atttctgcat ataaatattt    180
ctgcatataa attgtaactg atgtaagagg tttcatattg ctaatagcag ctacaatcca    240
gctaccattc tgcttttatt ttatggttgg gataaggctg gattattctg agtccaagct    300
aggccctttt gctaatcatg ttcataccte ttatcttcct cccacagctc ctgggcaacg    360
tgctggtctg tgtgctggcc catcactttg gcaaagaatt                          400
```

<210> SEQ ID NO 8
<211> LENGTH: 36
<212> TYPE: DNA
<213> ORGANISM: Artificial Sequence
<220> FEATURE:
<223> OTHER INFORMATION: Sequence encoding 5' UTR sequence

<400> SEQUENCE: 8

```
gggagcagcc acgggtcagc cacaagggcc acagcc                               36
```

<210> SEQ ID NO 9
<211> LENGTH: 589
<212> TYPE: DNA
<213> ORGANISM: Artificial Sequence
<220> FEATURE:
<223> OTHER INFORMATION: Sequence encoding WPRE

<400> SEQUENCE: 9

```
aatcaacctc tggattacaa aatttgtgaa agattgactg gtattcttaa ctatgttgct      60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact     240
ggttggggca ttgccaccac ctgtcagctc ctttccggga cttcgctttt ccccctccct    300
attgccacgg cggaactcat cgccgcctgc cttgcccgct gctggacagg gctcggctg     360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 10
<211> LENGTH: 18
<212> TYPE: DNA

```
<213> ORGANISM: Artificial Sequence
<220> FEATURE:
<223> OTHER INFORMATION: Ribozyme-specific RT primer

<400> SEQUENCE: 10
atgtgctgca aggcgatt                                                   18

<210> SEQ ID NO 11
<211> LENGTH: 20
<212> TYPE: DNA
<213> ORGANISM: Artificial Sequence
<220> FEATURE:
<223> OTHER INFORMATION: Rhodopsin RNA specific 5' primer

<400> SEQUENCE: 11
ctactcagcc ccagcggagg                                                 20

<210> SEQ ID NO 12
<211> LENGTH: 19
<212> TYPE: DNA
<213> ORGANISM: Artificial Sequence
<220> FEATURE:
<223> OTHER INFORMATION: Rhodopsin RNA specific 3' primer

<400> SEQUENCE: 12
tgtaaaacga cggccagtg                                                  19

<210> SEQ ID NO 13
<211> LENGTH: 14
<212> TYPE: DNA
<213> ORGANISM: Artificial Sequence
<220> FEATURE:
<223> OTHER INFORMATION: Synthetic construct

<400> SEQUENCE: 13
cgtactccgc ccaa                                                       14

<210> SEQ ID NO 14
<211> LENGTH: 9
<212> TYPE: RNA
<213> ORGANISM: Artificial Sequence
<220> FEATURE:
<223> OTHER INFORMATION: P1 sequence

<400> SEQUENCE: 14 cccgcccaa                                                              9

<210> SEQ ID NO 15
<211> LENGTH: 7
<212> TYPE: RNA
<213> ORGANISM: Artificial Sequence
<220> FEATURE:
<223> OTHER INFORMATION: P10 sequence

<400> SEQUENCE: 15 cguacuc                                                                7

<210> SEQ ID NO 16
<211> LENGTH: 7
<212> TYPE: RNA
<213> ORGANISM: Artificial Sequence
<220> FEATURE:
<223> OTHER INFORMATION: P10 sequence

<400> SEQUENCE: 16 gaguacg                                                                7
```

```
<210> SEQ ID NO 17
<211> LENGTH: 6
<212> TYPE: RNA
<213> ORGANISM: Artificial Sequence
<220> FEATURE:
<223> OTHER INFORMATION: Kozak sequence

<400> SEQUENCE: 17 cccacc                                                                    6

<210> SEQ ID NO 18
<211> LENGTH: 6
<212> TYPE: RNA
<213> ORGANISM: Artificial Sequence
<220> FEATURE:
<223> OTHER INFORMATION: Internal Guide Sequence

<400> SEQUENCE: 18 gcccaa                                                                    6

<210> SEQ ID NO 19
<211> LENGTH: 12
<212> TYPE: DNA
<213> ORGANISM: Artificial Sequence
<220> FEATURE:
<223> OTHER INFORMATION: Synthetic construct

<400> SEQUENCE: 19
gctcccgccc aa                                                            12

<210> SEQ ID NO 20
<211> LENGTH: 26
<212> TYPE: RNA
<213> ORGANISM: Artificial Sequence
<220> FEATURE:
<223> OTHER INFORMATION: RHO mRNA target site-containing region

<400> SEQUENCE: 20
cagcauucuu ggugggagc agccac                                              26

<210> SEQ ID NO 21
<211> LENGTH: 9
<212> TYPE: RNA
<213> ORGANISM: Artificial Sequence
<220> FEATURE:
<223> OTHER INFORMATION: P1 sequence

<400> SEQUENCE: 21 uccgcccaa                                                                 9
```

TRANS-SPLICING RIBOZYME TARGETING RHODOPSIN TRANSCRIPT AND USES THEREOF

CROSS REFERENCE TO RELATED APPLICATIONS

This application is a Continuation-in-part of PCT/KR2021/009555 filed Jul. 23, 2021, which claims priority based on Korean Patent Application Nos. 10-2020-0092265 filed Jul. 24, 2020 and 10-2021-0096986 filed Jul. 23, 2021, which are incorporated herein by reference in their entireties.

SEQUENCE LISTING

The content of the electronically submitted sequence listing, file name: Sequence_Listing_As_Filed_20211226.txt; size: 11,348 bytes; and date of creation: Dec. 26, 2021, filed herewith, is incorporated herein by reference in its entirety.

TECHNICAL FIELD

The present disclosure relates to a trans-splicing ribozyme that targets rhodopsin transcript and uses thereof.

BACKGROUND

Retinitis pigmentosa (RP) is a disease of the retina. It occurs due to a malfunction of photoreceptors in the retina. It is a hereditary and progressive disease in which the function of the retina, which plays a role in converting the light into electrical signals, is lost. It is characterized by progressive retinal degeneration. In the early stages of the disease, rod photoreceptor cells are damaged leading to night blindness, which suggests impairment of cell function. As the disease progresses, the visual field gradually narrows, peripheral vision may be completely lost, and ultimately, blindness may occur. Currently, no cure is available, and only treatment for retinitis pigmentosa is limited to slowing vision loss.

Retinitis pigmentosa is caused by genetic mutations in a wide variety of retinal photoreceptors. Inheritance can be autosomal dominant/recessive or X-linked. Autosomal dominant RP (ADRP, Autosomal Dominant Retinitis Pigmentosa) represent 15 to 25% of all RP cases. A large number of gene mutations are known to be associated with ADRP. Among them, mutations in the rhodopsin (RHO) gene account for about 30% of cases.

Rhodopsin is a G-protein coupled receptor (GPCR) present in the rod cells of the retina. As one of the light receptors, they help convert the light coming through the eye into an electrical signal and is required for enabling vision in the dark (low-light) conditions. Mutations in the RHO gene lead to functional abnormalities and deaths of rod cells, followed by rod-cone morphological abnormalities and cone cell dysfunction and death. Mutations in the RHO gene that induce RP are autosomal dominant mutation (ADRP) that cause vision loss. These mutations induce retinal degeneration and cause retinitis pigmentosa. Over 150 different missense/nonsense, insertion/deletion and splice site mutations are known as ADRP-inducing RHO mutations, and new mutations are still being reported (Non-Patent Document 1).

Among the various RHO gene mutations, the P23H mutation is the most common in ADRP patients. This mutation disrupts the folding of the RHO protein. As a result, the RHO protein is not transported to cell membrane, disrupting visual circuitry and light energy transport. Removal of the mutant allele and restoration of the normal wild-type (WT) allele expression could represent an important therapeutic strategy for treatment of ADRP.

LUXTURNA™ is used for the treatment of Leber congenital amaurosis (LCA) and autosomal recessive RP. LUXTURNA™ targets the mutation of RPE65 that has a function of maintaining photoreceptors in the eyeball. LUXTURNA™ has a limitation that it works only in patients with RPE65 gene mutation. Therefore, there is a need for other or new treatments for treating RP patients with mutant RHO gene.

Application of the CRISPR/cas9 system for gene editing may be possible for ADRP treatment. However, the CRISPR/cas9 system can edit a single gene mutation only. A dual delivery system for delivering a normal RHO gene is required. In addition, to correct multiple mutations, a plurality of different sgRNAs each of which target individual mutation are required. In other words, a separate system is needed to correct each individual mutation. The CRISPR/cas9 system has an additional drawback of introducing and expressing a foreign protein, such as cas9, which has a potential to induce immune response.

Gene silencing technology using siRNA/antisense RNA may be considered as another treatment option for development. However, similarly to CRISPR/cas9 system, siRNA/antisense RNA targets only a single mutation and furthermore it does not restore the RHO gene to normal. Therefore, an siRNA/antisense RNA targeting both normal and mutated RHO genes can be considered. However, this siRNA/antisense RNA system also requires a separate introduction of WT RHO gene.

As described above, an RNA-targeted method employing an antisense and a siRNA/shRNA and a gene editing method are currently under developments as treatments for RHO-ADRP. In conclusion, to overcome the drawback of these methods and to provide an ADRP treatment, a separate system for inducing WT RHO RNA expression is required.

The present inventors, as results of extensive research, developed a system capable of deleting various RHO transcripts and at the same time restoring WT RHO gene expression, by employing trans-splicing ribozyme.

[Reference Document] Non-Patent Document 1: Athanasiou, D., Aguila, M., Bellingham, J., Li, W., McCulley, C., Reeves, P. J., & Cheetham, M. E. (2018), The molecular and cellular basis of rhodopsin retinitis pigmentosa reveals potential strategies for therapy. Progress in retinal and eye research, 62, 1-23; doi.org/10.1016/j.preteyeres.2017.10.002.

DETAILED DESCRIPTION

It is an object of the present disclosure to provide a trans-splicing ribozyme system that targets a rhodopsin transcript and at the same time induces wild-type (WT) RHO transcript expression.

Another object of the present disclosure is to provide a gene delivery system comprising the trans-splicing ribozyme system.

According to an aspect of the present disclosure, a nucleic acid molecule comprising a first sequence encoding trans-splicing ribozyme, a second sequence encoding wild-type (WT) rhodopsin (RHO), and a third sequence expressing an RNA transcript comprising a binding site for RHO transcript. In another object of the present disclosure, the nucleic acid molecule further comprises an expression promoter for expressing the trans-splicing ribozyme.

Another aspect of the present disclosure is to provide a recombinant expression vector comprising the nucleic acid molecule. In another aspect of the present disclosure, a recombinant virus comprising the nucleic acid molecule is provided.

According to another aspect of the present disclosure, a pharmaceutical composition for preventing or treating retinitis pigmentosa comprising the trans-splicing ribozyme system, the genetic construct, the recombinant expression vector, or the recombinant virus as an active ingredient is provided.

According to still another aspect of the present disclosure, a method for preventing or treating retinitis pigmentosa by administering the composition to a subject in need thereof, is provided.

However, the technical problem to be solved by the present disclosure is not limited to the above and encompasses subject matter not specifically mentioned here as will be clearly understood by those skilled in the art.

An embodiment of the present disclosure provides a nucleic acid comprising a sequence encoding a rhodopsin-targeting ribozyme, in which the rhodopsin targeting ribozyme is capable of splicing at a specific site ("target splicing site") of a rhodopsin transcript and comprises sequences complementarily binding to a specific binding site(s) ("target binding site") of a target rhodopsin transcript, wherein the target binding site of the target rhodopsin transcript may span 5-10 nt and includes the target splicing site of a single nucleotide. The cleavage or splicing produces two spliced products: 5'-end side fragment and 3'-end side fragment. The nucleic acid may comprise a sequence encoding a normal wild-type (WT) transcript that is ligated to the cleaved site of the target transcript to replace the 3'-end side fragment.

In another embodiment, a ribonucleic acid molecule comprising a sequence capable of binding to a specific site(s) of a target transcript, wherein the ribonucleic acid is capable of cleaving the target transcript at the specific site, is provided. The cleavage or splicing produces two spliced products: 5'-end fragment (upstream fragment from the cleaved site) and 3'-end side fragment (downstream fragment). The ribonucleic acid molecule may further comprise a wild-type (WT) transcript sequence which is to be ligated to 3'-end at the cleaved specific site of the target transcript to replace the 3'-end side fragment.

In an embodiment, the present disclosure provides trans-splicing ribozymes targeting a rhodopsin transcript. Specifically, it provides trans-splicing ribozymes capable of targeting a rhodopsin transcript and simultaneously inducing WT RHO transcript expression.

In one embodiment of the present disclosure, the trans-splicing ribozyme may have a structure of 5'-IGS (internal guide sequence)-Ribozyme*-3', wherein the IGS sequence comprises site(s) capable of complementarily binding to and splice at a site(s) of a target transcript(s).

In another embodiment of the present disclosure, the trans-splicing ribozyme may further contain an exon region at its 3' end. That is, an exon is connected to the 3-end of 5'-IGS (internal guide sequence)-Ribozyme*-3', forming 5'-IGS (internal guide sequence)-Ribozyme*-exon-3'. The exon may comprise a WT rhodopsin gene transcript.

In another embodiment of the present disclosure, the IGS region is an oligonucleotide of 5 to 10 nucleotides (nt) in length capable of specifically binding to and forming G/U wobble base pairs with a target rhodopsin transcript (RNA) at a target site(s) in the target rhodopsin transcript.

Specifically, the IGS may comprise a nucleotide sequence of 5-10 nt in length capable of complementarily binding and forming G/U wobble base pairs at the target RHO transcript at specific site (also sometime referred to as "target site" or "binding site") comprising nucleotides at the following positions: +30, +35, +42, +43, +52, +54, +55, +59, +75, +97, +116, +122, +123, +127, +132, +140, +154, +165, +171, +187, +191, +207, +215, +222, +230, +232, +244, +256, +262, +273, +298, +308, +381, +403, +661 or +688, wherein the positions are identified with respect to the sequence of WT rhodopsin gene of SEQ ID NO: 1. In an embodiment, the IGS may bind to the target RHO transcript at site comprising a nucleotide at position +59. In embodiments, the IGS may comprise 5-10 nt, 5-9 nt, 5-8 nt, 5-7 nt, 5-6 nt, 6-10 nt, 6-9 nt, 6-8 nt, 6-7 nt, 7-10 nt, 7-9 nt, 7-8 nt, 8-10 nt, 8-9 nt, 9-10 nt, 5 nt, 6 nt, 7 nt, 8 nt, 9 nt, or 10 nt, in length.

In another embodiment of the present disclosure, the target rhodopsin transcript may contain one or more mutations. In still another embodiment, the target rhodopsin transcript may contain no mutation.

The rhodopsin mutation(s) may a mutation(s) at any one or more bases at positions 1 to 1142 of the wild-type rhodopsin transcript encoded by the gene of SEQ ID NO: 1. Specifically, the rhodopsin mutation(s) may include one or more known mutation(s) selected from the group consisting of the following or a mutation to be discovered in the future:

L328P, T342M, Q344R/P/ter, V345L/M, A346P, P347A/R/Q/L/S/T, ter349/Q/E, N15S, T17M, V20G, P23A/H/L, Q28H, G51R/V, P53R, T58R/M, V87D/L, G89D, G106R/W, C110F/R/S/Y, E113K, L125R, W161R, A164E/V, C167R/W, P171Q/L/S, Y178N/D/C, E181K, G182S/V, C185R, C187G/Y, G188R/E, D190N/G/Y, H211R/P, C222R, P267R/L, 5270R, K296N/E/M, R135G/L/P/W, T4K, T17M, M39R, N55K, G90V, M44T, V137M, G90D, T94I, A292E, A295V, F45L, V209M, F220C, P12R, R21C, Q28H, L40R, L46R, L47R, F52Y, F56Y, L57R, Y60ter, Q64ter, R69H, N78I, L79P, L88P, T92I, T97I, V104F, G109R, G114D/V, E122G, W126L/ter, S127F, L131P, Y136ter, C140S, T160T, M163T, A169P, P170H/R, S176F, P180A/S, Q184P, S186P/W, Y191C, T193M, M207R/K, V210F, I214N, P215L/T, M216R/L/K, R252P, T289P, S297R, A298D, K311E, N315ter, E341K, S343C, and Q312ter.

In an embodiment, the ribozyme may target, but not limited to, a rhodopsin P23H mutant transcript (rhodopsin transcript with P23H mutation). The rhodopsin P23H mutation has histidine instead of proline at position 23 with respect to the normal rhodopsin protein.

The trans-splicing ribozyme may comprise or consist of any one of the nucleotide sequences represented by SEQ ID NO: 2 to SEQ ID NO: 4.

In addition, the trans-splicing ribozyme of the present invention include sequences with sequence identify of 70% or more, 80% or more, 90% or more, 91% or more, 92% or more, 93% or more, 94% or more, 95% or more, 96% or more, 97% or more, 98% or more, or 99% or more to the nucleotide sequence of any one of SEQ ID NOs: 2 to 4.

In an embodiment of the present disclosure, the trans-splicing ribozyme may further comprise an antisense (AS) sequence linked to the 5'-end of the ribozyme.

The antisense sequence (AS) may be a sequence complementary to the target rhodopsin transcript(s). In an embodiment, the AS sequence may be complementary to a region of the target rhodopsin transcript(s) downstream from the target binding site to which the IGS binds.

In another embodiment of the present invention, the length of the AS may be 10 to 210 nt in length, and preferably, about 50 to about 150 nt, about 55 to about 150 nt, about 60 to about 150 nt, about 65 to about 150 nt, about 70 to about 150 nt, about 80 to about 150 nt, about 90 to about 150 nt, about 100 to about 150 nt, about 50 to about 160 nt, about 55 to about 160 nt, about 60 to about 160 nt, about 65 to about 160 nt, about 70 to about 160 nt, about 80 to about 160 nt, about 50 to about 170 nt, about 55 to about 170 nt, about 60 to about 170 nt, about 65 to about 170 nt, about 70 to about 170 nt, about 80 to about 170 nt, about 60 to about 180 nt, about 70 to about 180 nt, about 80 to about 180 nt, about 80 to about 180 nt, about 50 to about 140 nt, or about 50 to about 130 nt in length.

In one exemplary embodiment of the present disclosure, a trans-splicing ribozyme construct comprises an internal guide sequence (IGS) region consisting of or comprising SEQ ID NO: 18 (5'-GCCCAA-3') or a fragment of the sequence of SEQ ID NO: 13 or SEQ ID NO: 19.

According to another embodiment of the present disclosure, the trans-splicing ribozyme construct may have one of the following structures: 5'-IGS-Ribozyme*-3'; or 5'-AS-IGS-Ribozyme*-3'; or 5'-IGS-Ribozyme*-exon-3'; or 5'-AS-IGS-Ribozyme*-exon-3'.

In another embodiment of the present disclosure, a sequence of 5 to 20 random nucleotides may be included between the IGS region and the AS region, wherein the random nucleotide sequence may be a recognition sequence for a restriction enzyme, and the random nucleotide sequence may be preferably 8 nt (nucleotide) in length, and may comprise the P1 sequence (e.g., 5'-CCCGCCCAA-3' (SEQ ID NO: 14) or 5'-UCCGCCCAA-3' (SEQ ID NO: 21)) or P10 sequence (e.g., 5'-CGUACUC-3' (SEQ ID NO: 15) and/or 5'-GAGUACG-3' (SEQ ID NO: 16)) depicted in FIG. 4.

In another embodiment of the present disclosure, the Ribozyme* region may comprise or consist of the sequence of SEQ ID NO: 5.

In another embodiment, the Ribozyme* encompasses a sequence having at least 70%, at least 80%, at least 90%, at least 91%, at least 92%, at least 93%, at least 94%, at least 95%, at least 96%, at least 97%, at least 98%, at least 99% sequence identity to SEQ ID NO: 5.

In another embodiment of the present disclosure, the exon region may contain all or part of the normal WT RHO transcript sequence or all or part of an optimized RHO transcript sequence. In an embodiment, a nucleotide molecule comprising sequences encoding the trans-splicing ribozyme described above is also provided.

Ribozyme(s) and Trans-Splicing Ribozyme(s)

As used herein, "ribozyme" means an RNA molecule that acts like an enzyme or a molecule comprising a protein and an RNA molecule wherein RNA molecule acts like an enzyme, also known as catalytic RNA. RNA molecules with a specific tertiary structure have catalytic or autocatalytic properties, and some ribozymes inhibit activity of other RNA molecules by cleaving them while some ribozymes can inhibit their own activity by self-cleavage. Other ribozymes catalyze ribosome aminotransferase activity. These ribozymes include hammerhead ribozymes, a VS ribozyme, and hairpin ribozymes.

Embodiments of the present invention encompasses a ribozyme having a trans-splicing function, more specifically, trans-splicing ribozymes targeting specific variants of rhodopsin transcript.

In embodiments of the present invention, "trans-splicing ribozyme" means a ribozyme (or a ribozyme construct) comprising an internal guide sequence (IGS) and a 3' exon, wherein the IGS recognizes and binds a target RNA (present separately from the ribozyme) at a specific site, cleaves the target RNA and links the 3' exon of the ribozyme immediately after the cleavage site of the target RNA.

In the present specification, the ribozyme sequence may be represented by DNA sequence that encodes the ribozyme or a corresponding RNA sequence. When represented by a DNA sequence, it would be obvious to one of ordinary skill in the art that an RNA sequence corresponding to the DNA sequence is also within the scope of the present invention.

In the present specification, "rhodopsin transcript(s)," "RHO transcript(s)" or "RHO RNA" means RNA molecules produced by transcription of the WT rhodopsin gene or a mutant rhodopsin gene, or a mixture thereof. In the present specification, "mutant rhodopsin transcript," "mutant RHO transcript" or "mutant RHO RNA" means RNA molecules produced by transcription of a mutant rhodopsin gene (i.e., rhodopsin gene with a mutation(s)). Mutant RHO transcripts may be referred to according to the specific mutation(s) they carry, for example, "P23H RHO." Normal rhodopsin transcript may be referred to as "WT RHO transcript," "WT RHO" or "WT RHO RNA."

According to the embodiments, the trans-splicing ribozyme described herein may bind and splice target rhodopsin transcripts that may or may not contain a mutation and replace the cleaved fragment downstream from the cleavage site with a normal WT rhodopsin transcript that is a part of the trans-splicing ribozyme. The term "target transcript," "target RNA," "target RHO transcript," "target rhodopsin transcript," or "target RHO RNA," used herein, refers to transcripts or expression products present in a sample or in a subject and not a part of the transcript (or transgene) forming a part of the trans-splicing ribozyme. Therefore, the term "rhodopsin transcript(s)," "RHO transcript(s)" or "RHO RNA," as used herein, encompasses WT RHO transcript and mutant RHO transcript, unless specified otherwise. The term "transcript" (or 'transgene") used to refer to an element or a sequence in the trans-splicing ribozyme refers to a desired transcript that is intended to be ligated to the 3-end of the upstream spliced product of the target transcript.

In some embodiments, the trans-splicing ribozyme targeting at least one of the mutant rhodopsin transcript sites is a ribozyme that has been genetically engineered to selectively recognize and bind to a mutant rhodopsin RNA involved in retinitis pigmentosa and trigger a trans-splicing reaction when introduced into a cell. It can be manufactured by any suitable method known in the art. For example, a complementary sequence specific for a conserved region of the target RNA may be linked at the 5' end of the ribozyme making the ribozyme to have specificity to the target RNA.

Rhodopsin and Rhodopsin Mutations

A lot of information on rhodopsin mutant genes is known in the field, as summarized, for example, the above-mentioned Non-patent document 1 and website at www.retina-international.org/files/sci-news/rhomut.htm.

In embodiment of the present invention, a trans-splicing ribozyme that targets rhodopsin transcripts and replaces the target rhodopsin with the normal (WT) rhodopsin (FIG. 1) is provided. A nucleic acid molecule encoding the trans-splicing ribozyme, a vector, and a delivery system to deliver the trans-splicing ribozyme or its gene is disclosed RHO mutations causing functional abnormalities occur predominantly downstream of the 5'-UTR region. The trans-splicing ribozyme according to embodiments of the present invention targets the 5'-UTR region to excise the RHO transcript region that is downstream of 5'-UTR and contains the mutation site(s) and at the same time replaces the excised RHO transcript region with a WT RHO transcript. Thus, the trans-splicing ribozyme according to the embodiments of the present invention may be used to treat or prevent RHO mutation-associated diseases such as RP regardless of mutation types.

In addition, it is possible that the trans-splicing ribozyme according to embodiments of the present invention targets the normal rhodopsin transcript. However, in this case, since the transcript is replaced with a normal rhodopsin transcript, the trans-splicing ribozymes does not affect normal rhodopsin.

The rhodopsin mutation(s) may a mutation(s) at any one or more bases at positions 1 to 1142 of the wild-type rhodopsin transcript encoded by the gene of SEQ ID NO: 1. Specifically, the rhodopsin mutation(s) may include one or more known mutation(s) selected from the group consisting of the following or a mutation to be discovered in the future:

L328P, T342M, Q344R/P/ter, V345L/M, A346P, P347A/R/Q/L/S/T, ter349/Q/E, N15S, T17M, V20G, P23A/H/L, Q28H, G51R/V, P53R, T58R/M, V87D/L, G89D, G106R/W, C110F/R/S/Y, E113K, L125R, W161R, A164E/V, C167R/W, P171Q/L/S, Y178N/D/C, E181K, G182S/V, C185R, C187G/Y, G188R/E, D190N/G/Y, H211R/P, C222R, P267R/L, 5270R, K296N/E/M, R135G/L/P/W, T4K, T17M, M39R, N55K, G90V, M44T, V137M, G90D, T94I, A292E, A295V, F45L, V209M, F220C, P12R, R21C, Q28H, L40R, L46R, L47R, F52Y, F56Y, L57R, Y60ter, Q64ter, R69H, N78I, L79P, L88P, T92I, T97I, V104F, G109R, G114D/V, E122G, W126L/ter, S127F, L131P, Y136ter, C140S, T160T, M163T, A169P, P170H/R, S176F, P180A/S, Q184P, S186P/W, Y191C, T193M, M207R/K, V210F, I214N, P215L/T, M216R/L/K, R252P, T289P, S297R, A298D, K311E, N315ter, E341K, S343C, and Q312ter.

In an embodiment, the ribozyme may target, but not limited to, a rhodopsin P23H mutant transcript (rhodopsin transcript with P23H mutation). The rhodopsin P23H mutation has histidine instead of proline at position 23 with respect to the normal rhodopsin protein.

Gene Delivery

In one aspect, the present invention comprises non-viral gene delivery systems for trans-splicing ribozymes whereby the trans-splicing ribozyme is loaded into a non-viral gene carrier and delivered directly into a living cell.

The non-viral gene carrier may be a liposome or lipid nanoparticles, but is not limited thereto. Any suitable delivery method known in the art may be used.

The liposome may be LIPOFECTAMINE® LTX, LIPOFECTAMINE® 2000, or LIPOFECTAMINE® 3000, LIPOFECTIN®, CELLFECTIN®, LIPOFECTACE®, DMRIE-C®, RNAIMAX®, DOTAP®, SAINT-RED®, AVALANCHE-OMNI®, EXPLEX®, POLYFECT®, SUPERFECT®, EFFECTENE®, ATTRACTENE® OR HIPERFECT®. Other commercially available liposomes may also be used without restrictions.

Lipid nanoparticles include a drug and phospholipids. The phospholipids encapsulate a core formed from ionizable lipids and drug(s). They fuse to the phospholipid bilayer of the target cell and pass through the cell membrane enabling intracellular delivery of drugs and facilitating endosomal escape.

A phospholipid that can promote the fusion of lipid nanoparticles to bilayer membranes may include, but are not limited to: dioleoylphosphatidylethanolamine (DOPE), distearoylphosphatidylcholine (DSPC), palmitoyloleoylphosphatidylcholine (POPC), egg phosphatidylcholine (EPC), dioleoylphosphatidylcholine (DOPC), dipalmitoylphosphatidylcholine (DPPC), dioleoylphosphatidylglycerol (DOPG), dipalmitoylphosphatidylglycerol (DPPG), distearoylphosphatidylethanolamine (DSPE), Phosphatidylethanolamine (PE), dipalmitoylphosphatidylethanolamine, 1,2-dioleoyl-sn-glycero-3-phosphoethanolamine, 1-palmitoyl-2-oleoyl-sn-glycero-3-phosphoethanolamine (POPE), 1-palmitoyl-2-oleoyl-sn-glycero-3-phosphocholine (POPC), 1,2-dioleoyl-sn-glycero-3-[phospho-L-serine] (DOPS), and 1,2-dioleoyl-sn-glycero-3-[phospho-L-serine]. One or more of these phospholipids may be used.

Cationic lipid transporters include a complex formed from gene molecules, expression vectors carrying a gene, or a nucleic acid molecule, which are negatively charged, and nano-sized liposomes (of cationic lipids) or lipid nanoparticles, which are positively charged. The complex is delivered into cells by phagocytosis. The complex is delivered into the cell in an endosome and is transferred into a lysosome and then exits into the cytoplasm and is expressed. Another method of delivery of nucleic acids into the cells use cationic polymers and are similar to the cationic lipid transporters, except for employing the cationic polymers in place of the cationic lipids. Representative cationic polymers include polyethylenimine, poly-L-lysine, chitosan, and the like.

The trans-splicing ribozyme according to embodiments of the present invention, which carries the desired gene such as a normal wild-type rhodopsin, can be loaded into a non-viral gene delivery system. The trans-splicing ribozyme loaded into a non-viral gene delivery system such as lipid nanoparticle or liposomes can be delivered to the target cells or tissues where a normal rhodopsin gene can be introduced to a target site of the RHO transcript in the cells or tissues.

Expression Vector and Recombinant Adeno-Associated Viruses (AAVs)

In another aspect, the present invention provides a gene construct comprising the trans-splicing ribozyme. The gene construct comprises a desired gene in the 3' exon region of the ribozyme.

The desired gene may be a normal rhodopsin gene and/or a reporter gene.

The reporter gene may be luciferase, green fluorescent protein (GFP), modified green fluorescent protein (mGFP), enhanced green fluorescent protein (EGFP), red fluorescent protein (RFP), modified red fluorescent protein (mRFP), enhanced red fluorescent protein (ERFP), blue fluorescent protein (BFP), enhanced blue fluorescent protein (EBFP), yellow fluorescent protein (YFP), enhanced yellow fluorescent protein (EYFP), or any other suitable reporter gene known in the art.

By inserting a reporter gene as a desired gene, the expression level of rhodopsin transcript may be observed.

The gene construct may comprise an operably linked promoter sequence.

The promoter may be promoter of prokaryotic cells or mammalian viruses such as CMV promoter (cytomegalovirus promoter), CAG promoter (CMV early enhancer element+chicken beta-actin promoter/splicing donor (SD)+rabbit beta-globin splicer acceptor (SA)), SV40 promoter, adenovirus promoter (major late promoter), pLλ promoter, trp promoter, lac promoter, tac promoter, T7 promoter, vaccinia virus 7.5K promoter, HSV tk promoter, SV40E1 promoter, respiratory syncytial virus (RSV) promoter, and LTR promoter, or promoter of mammalian cells such as metallothionein promoter, beta-actin promoter, ubiquitin C promoter, EF1-alpha (elongation factor 1-alpha) promoter, IL-2 (interleukin-2) gene promoter, lymphotoxin gene promoter, and GM-CSF (granulocyte-macrophage colony stimulating factor) gene promoter, or retinal tissue-specific promoter such as RHO (rhodopsin) gene promoter, RK (rhodopsin kinase) gene promoter, and RedO (red opsin) gene promoter, or other suitable promoters.

As used herein, "gene construct" refers to a construct comprising an element to enhance specificity to target site(s) of target rhodopsin transcript(s). In particular, the gene construct may contain a sequence(s) encoding the trans-splicing ribozyme according to embodiments.

An antisense sequence linked to the trans-splicing ribozyme of the gene construct may increase specificity of ribozyme for the target rhodopsin transcript and, thus, enhance the therapeutic effect. Any sequence intended for achieving this purpose may be included without limitation.

The construct according to embodiments of the present invention targets a rhodopsin transcript and also contains an antisense sequence specific for the targeted rhodopsin transcript, and, thus, can be specifically expressed only in cells in which rhodopsin is expressed.

FIG. 2 depicts a gene construct according to one embodiment of the present invention, comprising a promoter, a trans-splicing ribozyme region, and a normal rhodopsin gene region.

In another aspect of the present invention a recombinant expression vector comprising the above-mentioned gene construct is provided.

In another aspect of the present invention a recombinant virus comprising the above-mentioned gene construct is provided.

The virus may be an adenovirus, adeno-associated virus (AAV), retrovirus, lentivirus, herpes simplex virus, or vaccinia virus, or any other suitable virus. Recombinant AAVs suitable for use in delivering a desired gene to the targeted cell or tissue are described in, for example, US 2003/0138772, US 2011/0171262, WO 2015/164786, the contents of which are incorporated herein by reference in their entireties.

As used herein, the term "vector" refers to a construct capable of expressing a desired protein in an appropriate host cell. An expression vector refers to a genetic construct comprising a gene insert operably linked to essential regulatory elements enabling its expression. In the present invention, the term, "operably linked" means a functional linkage between the expression regulatory sequence and the nucleic acid sequence encoding the desired transcript. For example, by operably linking the ribozyme coding sequence to a promoter, the expression of the ribozyme coding sequence is placed under the influence or control of this promoter. Operably linking the two sequences (the ribozyme coding sequence and the promoter region sequence at the 5' end of the ribozyme coding sequence) allows the ribozyme coding sequence to be transcribed by action of the promoter. If the linkage between the two sequences does not induce frame-shift mutations, and does not inhibit the expression regulatory sequence's function of controlling the ribozyme expression, the linkage is considered as "operably linked." Operable linkages within recombinant vectors are well known in the art. They can be prepared using known genetic recombination technology, e.g., using site-specific DNA enzymes for cleavage and ligation generally known in the art.

The vector of the present invention may include a promoter, an operator, a Kozak consensus sequence, a start codon, a stop codon, and other elements, such as polyadenylation signals, enhancers, membrane targeting sequence, signal sequence, or leader sequence for secretion, and may be prepared in various ways depending on the purpose. The promoter of the vector may be constitutive or inducible. In addition, the vector may contain a selectable marker for selecting host cells containing the construct, and, in the case of an expression vectors, an origin of replication. A vector may self-replicate or be incorporated into host DNA. The vector may be a plasmid vector, a cosmid vector, a viral vector, or another suitable vector.

If a vector is a viral vector, it may be derived from adenovirus, adeno-associated virus (AAV), retrovirus, lentivirus, herpes simplex virus, vaccinia virus, or other suitable viruses.

Another embodiment of the present invention is a transformed cell into which the recombinant vector is introduced.

As used herein, the term "introduction" refers to introducing a foreign gene into a cell. Constructs according to embodiments of the present invention may be introduced into a cell by transfection or transduction. Transfection may be performed by calcium phosphate-DNA co-precipitation, DEAE-dextran-mediated transfection, polybrene-mediated transfection, electroporation, microinjection, liposome fusion, lipofectamine, protoplast fusion and by various other methods known in the art. Transduction may be performed by means of infection with a virus wherein the viral particles are used to deliver genes into cells.

As used herein, the term "transformed cell" refers to a target cell into which the polynucleotide has been introduced.

Transformation can be accomplished by the methods enumerated above, or by another appropriate technique suitable for introducing genetic material into a host cell.

A transformed cell of the present invention may be obtained by introducing a recombinant vector containing a polynucleotide encoding a ribozyme targeting the rhodopsin transcript.

In one embodiment of the present invention, the recombinant virus is a recombinant adeno-associated viruses (AAV). In one embodiment of the present invention recombinant adeno-associated viruses (AAV) contains a polynucleotide sequence encoding a trans-splicing ribozyme operably linked to a promoter.

The recombinant AAV is a natural or an artificially derived serotype, isolate or a clade of AAV.

The polynucleotide sequence encoding the trans-splicing ribozyme may comprise or consist of any one of SEQ ID NOs: 2-5 and any sequences having sequence homology of 70% or more, 80% or more, or 90% or more, 91% or more, 92% or more, 93% or more, 94% or more, 95% or more, 96% or more, 97% or more, 98% or more, or 99% or more to any one of SEQ ID NOs: 2-5.

The promoter may be a constitutive or inducible promoter. Examples of constitutive promoter include, but are not limited thereto, a CMV promoter (optionally with the CMV enhancer), retroviral Rous sarcoma virus (RSV) LTR promoter (optionally with the RSV enhancer), SV40 promoter, dihydrofolate reductase promoter, (3-actin promoter, phosphoglycerol kinase (PGK) promoter, or EF1 a promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources such as Invitrogen. Examples of inducible promoters regulated by exogenously supplied promoters include the zinc-inducible sheep metal-lothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), the RU486-inducible system (Wang et al, Nat. Biotech., 15:239-243 (1997), and the rapamycin-inducible system (Magari et al, J. Clin. Invest., 100:2865-2872 (1997)).

In another embodiment, the native promoter, i.e., a RHO promoter, RK (GRK) promoter and RedO promoter may be used.

The recombinant AAV may further include regulatory sequences.

The regulatory sequence may be a splicing donor/splicing acceptor sequence (SD/SA) and/or a woodchuck hepatitis post-regulatory element (WPRE) sequence.

In the embodiments, the SD/SA can promote transcription initiation, processing of RNA polymerase II, and nucleocytoplasmic export of mRNA.

In the embodiments, WPRE sequence may be used to significantly increase the expression and function of ribozyme RNA by increasing the levels of pre-mRNA and/or promoting mRNA processing and transport from the nucleus to the cytoplasm.

The SD/SA sequence according to the present invention may correspond to the beginning and ending of the truncated intron that is spliced to be removed. The SD sequence may be a GU sequence at the 5' end of an intron and SA sequence may be an AG sequence at the 3' end of an intron.

WPRE according to the present invention refers to a sequence that increases the expression of a gene by forming a tertiary structure that promotes transcription of DNA.

In the embodiments, the SD/SA sequence and WPRE sequence may comprise or consist of SEQ ID NO: 7 and SEQ ID NO: 9, respectively, and may be present in the desired gene expression cassette. Other sequences promote gene expression may also be used.

The AAV may be either a naturally or artificially derived serotype or isolate or clade of AAV. Thus, the AAV genome may be a native AAV viral genome or it may be a genome or an artificially created AAV viral genome. As known to those skilled in the art, AAV viruses can be classified depend on various biological systems.

AAV viruses are generally referred to according to their serotype. The serotypes are distinguished from each other by the expression profile of their capsid surface antigens. Variant subspecies of AAV with unique reactivity may be used. In general, viruses with a specific AAV serotype are not cross-reactive with neutralizing antibodies specific for other AAV serotypes. AAV serotypes are AAV1, AAV2, AAV3, AAV4, AAV5, AAV6, AAV7, AAV8, AAV9, AAV10 and AAV11. Recombinant serotypes, such as Rec2 and Rec3, recently identified in the primate brain, are also included.

AAV serotypes of particular interest for use in the present invention are those able to infect ocular tissues, such as retinal pigment epithelium. AAV2, AAV5 and AAV8 are efficiently transduced into these tissues. A review of AAV serotypes is provided by Choi, V. W., et al. (2005), AAV hybrid serotypes: improved vectors for gene delivery. Current gene therapy, 5(3), 299-310 at doi.org/10.2174/1566523054064968; and Wu, Z. et al. (2006). Adeno-associated virus serotypes: vector toolkit for human gene therapy. Molecular therapy: the journal of the American Society of Gene Therapy, 14(3), 316-327, at doi.org/10.1016/j.ymthe.2006.05.009.

AAV viruses are also referred to in terms of clades or clones. Viruses in the same clade or clone have a natural or artificial phylogenetic relationships. A clade or a clone generally includes a phylogenetic family of AAV viruses that can be traced to a common ancestor. AAV viruses can be found in nature or artificially engineered as a specific isolate, such as a genetic isolate of a specific AAV virus. Genetic isolate refers to a distinct population of viruses that exhibit limited mixing with other virus populations and may be recognized at a genetic level.

In general, the genome of naturally occurring or artificially derived serotypes, isolates or strains of AAV comprises one or more inverted terminal repeat sequences (ITRs). The ITR sequence provides a functional origin of replication at the cis position, and allows for fusion and cleavage of vector to/from cell genomes. In some embodiments, one or more ITR sequences flank polynucleotide sequences encoding Rep-1 or a variant thereof.

The AAV genome also generally contains packaging genes, such as rep and/or cap genes, which encode proteins necessary for packaging of AAV viral particles. The rep gene encodes at least one of Rep78, Rep68, Rep52 and Rep40 or variants thereof. The AAV genome may also contain one or more cap gene, such as VP1, VP2 and VP3 or variants thereof. Cap genes encode a capsid protein. These proteins form the capsids of AAV viral particles. A promoter is operably linked to each packaging gene.

The AAV vectors may contain the entire genome of a natural or artificial AAV. A vector comprising the entire AAV genome may be prepared in vitro. Such vectors can in principle be administered to a patient. Preferably, the AAV genome is derivatised for administration to a patient. Such derivatisations are standard procedure in the art. In some embodiments of the present invention, a vector may be prepared by applying techniques known in the art including the use of derivatisations or modifications.

In another aspect, the present disclosure provides a method and a system for non-viral delivery of gene constructs discussed above.

The non-viral gene carrier may be liposomes or lipid nanoparticles, or other suitable non-viral delivery systems known in the art. Detailed description of such systems is not included here.

Compositions and Treatment Methods

In its various aspects, the present disclosure provides a ribozyme, a non-viral gene carrier, a gene construct, a recombinant expression vector or a pharmaceutical composition for preventing or treating retinitis pigmentosa.

In another aspect, the present invention provides a method for preventing or treating retinitis pigmentosa comprising the step of administering a pharmaceutical composition to a subject.

As used herein, the term "prevention" refers to any action that delays the onset of retinitis pigmentosa by administration of the pharmaceutical composition according to the present invention.

As used herein, the term "treatment" refers to any action that improves or beneficially changes the course of retinitis pigmentosa by the administration of a pharmaceutical composition of the present invention.

The pharmaceutical composition according to the present disclosure may further contain a pharmaceutically acceptable carrier, excipient or a diluent. Examples of pharmaceutically acceptable carriers, excipients and diluents include lactose, dextrose, sucrose, sorbitol, mannitol, xylitol, erythritol, maltitol, starch, acacia gum, alginate, gelatin, calcium phosphate, calcium silicate, calcium carbonate, cellulose, methyl cellulose, polyvinylpyrrolidone, water, methylhydroxybenzoate, propyl hydroxybenzoate, talc, magnesium stearate, mineral oil and others.

In other embodiments, a compositions of the present disclosure may contain the AAV alone or in combination with one or more other viruses (e.g., a second rAAV with one or more different transgenes). In some embodiments, the composition comprises 1, 2, 3, 4, 5, 6, 7, 8, 9, 10, or more different AAVs, each having one or more different transgenes. The composition also may contain a suitable carrier. For example, one suitable carrier comprise, but is not limited to, saline, which can be formulated with a variety of buffers (e.g., phosphate buffered saline). Other exemplary carriers include sterile saline, lactose, sucrose, calcium phosphate, gelatin, dextran, agar, pectin, peanut oil, sesame oil and water. The compositions may include other conventional pharmaceutical ingredients, such as preservatives or chemical stabilizers, in addition to AAV and carriers. Suitable exemplary preservatives include, but are not limited to, chlorobutanol, potassium sorbate, sorbic acid, sulfur dioxide, propyl gallate, parabens, ethylvanillin, glycerin, phenol and parachlorophenol. Suitable chemical stabilizers include gelatin and albumin.

The pharmaceutical composition of the present invention may be administered orally or parenterally. Parenteral administration is preferred. There are three routes for parenteral intraocular administration: intravitreal injection, suprachoroidal injection and subretinal injection.

According to one embodiment of the present disclosure, the pharmaceutical composition may be administered efficiently and directly to photoreceptor cells by a subretinal injection. The composition to be administered by injection may be dissolved in a sterile medium. Before administration by injection, distilled water may be added to obtain the appropriate concentration of the composition. In addition, when prepared as an injection, buffers, preservatives, analgesics, solubilizers, isotonic agents, stabilizers and other ingredients may be added. Compositions may be prepared and used in dosage forms, such as in single dose ampoules or in multiple doses.

AAV carrying the trans-splicing according to the embodiments can be used to remove a target RHO transcript and induce WT RHO in an episomal state, instead of directly inserting into human genome.

The dosage of the pharmaceutical composition of the present disclosure depends on the patient's condition and weight, disease stage and other drugs the patient may be taking. The dosage may vary depending on the form, administration route and timing, and may be appropriately determined by those skilled in the art. Pharmaceutical composition according to the present invention may be used alone or in combination with other therapeutic agents, or as an adjuvant, for example, after surgical treatment. The AAV carrying the trans-splicing ribozyme according to embodiments of the present disclosure may be administered in sufficient amounts to transfect cells in the desired tissue and to provide sufficient levels of gene delivery and expression without undue adverse effects. The unit of dose of AAV required to achieve a particular "therapeutic effect" can be expressed, for example, in the number of genomic copies per kilogram of body weight (GC/kg) of the AAV administered. It will vary based on several factors, including the pathway, the level of expression of the gene or RNA required to achieve a therapeutic effect, the particular disease or disorder being treated, and the stability of the gene or RNA. An effective amount of AAV is sufficient to infect the animal and target the desired tissue. For example, the effective amount of AAV is generally in the range of about 1 µl to about 100 ml of a solution containing about $10^7$ to $10^{16}$ genomic copies. Other volumes of solution and dosage may be used. The volume used will typically depend, among other things, on the size of the subject, the dose of the AAV, and the route of administration. AAV can be delivered to the subject according to any suitable method known in the art. AAV suspended in a carrier that is preferably physiologically compatible to a subject, such as a host animal, such as a human, mouse, rat, cat, dog, sheep, rabbit, horse, bovine, etc. It can be administered to goats, pigs, guinea pigs, hamsters, chickens, citrus butterflies, or non-human primates. In some embodiments, the subject is human.

Trans-splicing ribozyme according to the embodiments targets rhodopsin transcript and replaces it with normal (wild-type) rhodopsin RNA allowing the normal gene to be expressed. Therefore, trans-splicing ribozyme according to the embodiments may provide a curative treatment for retinitis pigmentosa. The target transcript may harbor any rhodopsin mutations. The trans-splicing ribozyme has the advantage of being applicable to all patients with various rhodopsin mutations by selecting a site of target rhodopsin transcript, which facilitates excision of rhodopsin transcript containing any mutations and replacing the excised transcript with a normal WT rhodopsin transcript. In addition, the expression of normal WT rhodopsin depends on the amount of target rhodopsin transcripts expressed in patient cells, adverse effects or toxicity caused by excessive expression of normal rhodopsin proteins can be minimized. Also the RNA restoration by trans-splicing ribozymes does not utilize endogenous cell machinery and the trans-splicing ribozyme system does not require introduction of an external protein to function within the cell. Therefore, trans-splicing ribozyme is safer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A is a schematic diagram showing the process of selection of target sites on RHO RNA through in vitro mapping and intracellular mapping and FIG. 3B shows the in vitro and in vivo (intracellular) mapping results.

In FIG. 4, the sequence cagcauucUUGGGUGGGagcagccac is represented by SEQ ID NO: 20 (underlined U" is at the position 59), the IGS sequences 5'-gcccaa-3' is represented by SEQ ID NO: 18. Kozak sequence 5'-cccacc-3' is represented by SEQ ID NO: 17. P1 sequences 5'-cccgcccaa-3' and 5'-uccgcccaa-3' are represented by SEQ ID NOs: 14 and 21, respectively, and P10 sequences 5'-cguacuc-3' and 5'-gaguacg-3' are represented by SEQ ID NOs: 15 and 16, respectively.

FIG. 6A-FIG. 6D depict the results of comparison of RHO targeting ribozyme constructs in 293A cells.

FIG. 7A and FIG. 7B show the results of an experiment confirming in vitro efficacy of the RHO targeting ribozyme using cell lines stably expressing the P23H mutant hRHO gene. FIG. 7A is nucleotide sequence analysis result confirming that trans-splicing (t/s) occurred at the target site. FIG. 7B is fluorescent microscopic photos showing the expression of ribozyme in the cells using an anti-RHO antibody and a secondary fluorescent-labeled antibody, which confirm that in the cells transfected with the RHO targeting ribozyme, RHO proteins were localized to the cell membrane, whereas the RHO proteins with P23H mutation were dispersed in cytosol.

FIG. 10A shows the result 2 weeks after administration, and FIG. 10B shows the result 5 weeks after administration.

(FIG. 11A is the result 2 weeks after administration, FIG. 11B is the result 5 weeks after administration).

MODES FOR CARRYING OUT THE EMBODIMENTS

Figure 1:
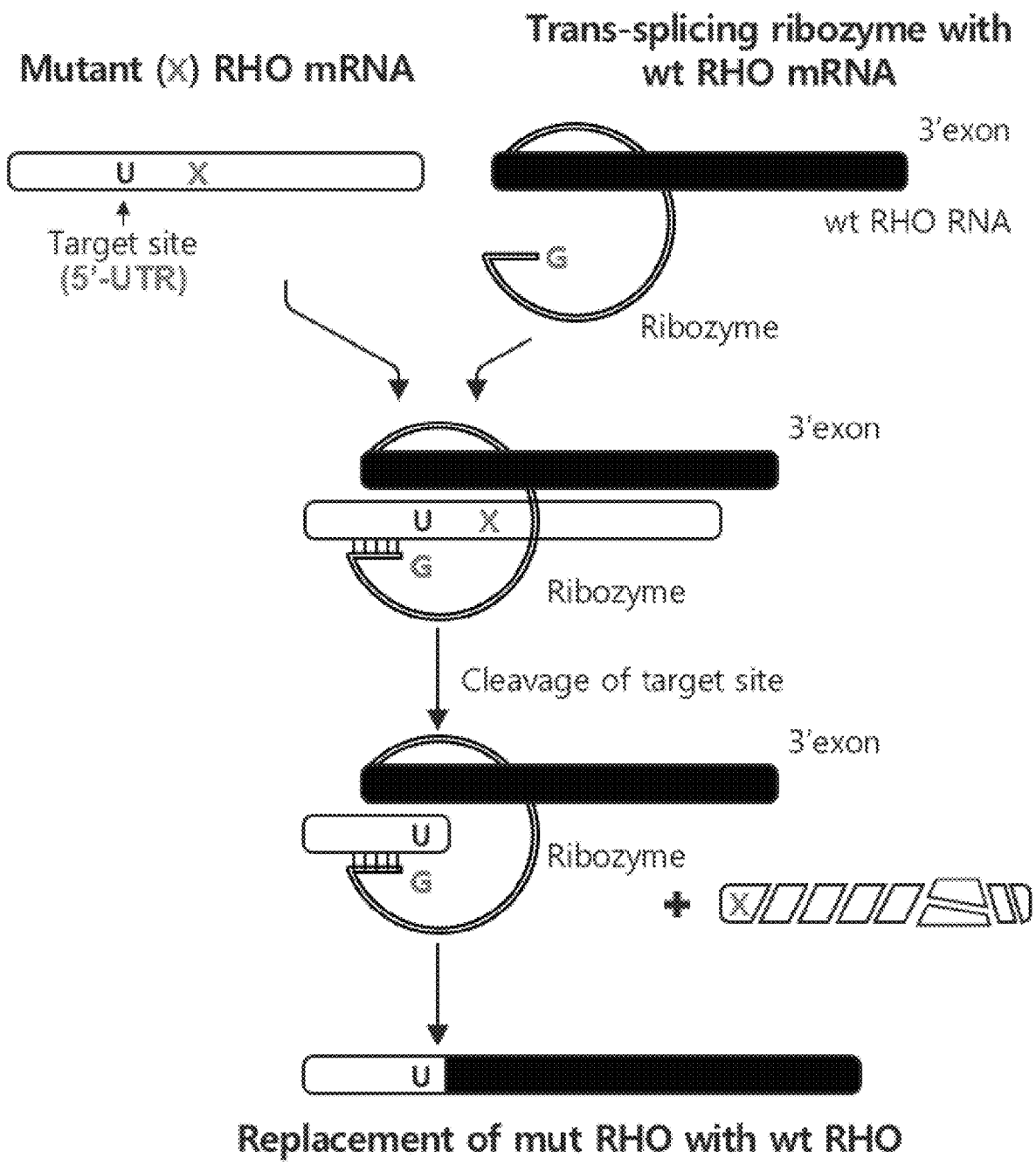
FIG. 1 is a schematic diagram showing the mechanism of trans-splicing ribozyme targeting RHO transcript according to an embodiment of the present invention.

The present invention has various embodiments which may include various modifications. Hereinafter, specific embodiments illustrated in the drawings are described in detail. However, this is not intended to limit the invention to specific embodiments. All modifications, equivalents and substitutes within the spirit and scope of the present invention should be understood to be included. When a detailed description of the technology may obscure the essence of the present invention, such description may be omitted.

Example 1: Design of Rhodopsin (RHO) RNA Targeting Trans-Splicing Ribozyme

Figure 2:
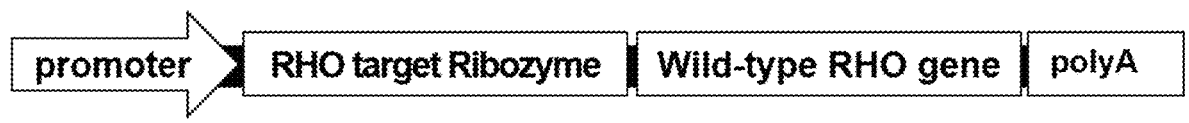
FIG. 2 is a schematic diagram showing a basic configuration of a gene construct comprising a ribozyme according to an embodiment of the present invention containing a promoter, trans-splicing ribozyme sequence, and normal (WT) rhodopsin gene sequence.

Sequences of RHO RNA variants were analyzed to select a target RNA site. Design of RHO targeting trans-splicing ribozyme is shown in FIG. 2.

Example 2: Selection of Target Site of Rhodopsin (RHO) RNA by In Vitro Mapping and Intracellular Mapping WT RHO RNA or P23H RHO RNA and ribozyme RNA library was used to perform in vitro mapping and intracellular mapping. A reaction was carried out by mixing the random ribozyme library RNA with Rhodopsin RNA in test tubes for in vitro mapping, RT-PCR was performed and then trans-splicing was performed through sequencing of PCR DNA bands expected as products. The target rhodopsin RNA site was identified.

More specifically, rhodopsin RNA is synthesized by in vitro transcription and trans-splicing ribozyme library RNA with a random sequence (G) at the 5' end is constructed. In vitro transcription was performed as follows: 0.1 pmol of rhodopsin RNA was added to 1× in vitro trans-splicing reaction Buffer (50 mM HEPES (pH 7.0), 150 mM NaCl, 5 mM MgCl2) to make a total of 10 μL. 1 pmole of ribozyme library RNA was added to mix with in vitro trans-splicing reaction buffer (1×) to make a total of 9 μL, then 1 μL of 1 mM GTP was added for the final concentration of 0.1 mM GTP in a separate tube. The two separate reactions were incubated at 95° C. for 1 minute and then at 37° C. for 3 minutes, respectively. The two reactions were then mixed and incubated at 37° C. for 3 hours. RNA was recovered from the reaction mix by phenol extraction/EtOH precipitation, and RT-PCR was performed.

A ribozyme-specific RT primer (5'-ATGTGCTGCAAGGCGATT-3') (SEQ ID NO: 10) was added, and cDNA was synthesized by reverse transcription in a total volume of 20 μL 35 cycles of PCR were carried out using 2 uL of cDNA, 10 pmol of rhodopsin RNA specific 5' primer (5'-CTACTCAGCCCCAGCGGAGG-3') (SEQ ID NO: 11), and 10 pmol of ribozyme specific 3' primer (RY-TS) (5'-TGTAAAACGACGGCCAGTG-3') (SEQ ID NO: 12) under the following cycling conditions: 95° C. 30 seconds, 55° C. for 30 seconds and 72° C. for 30 seconds. PCR products were separated by electrophoresis on a 2% TBE agarose gel.

Figure 3A:
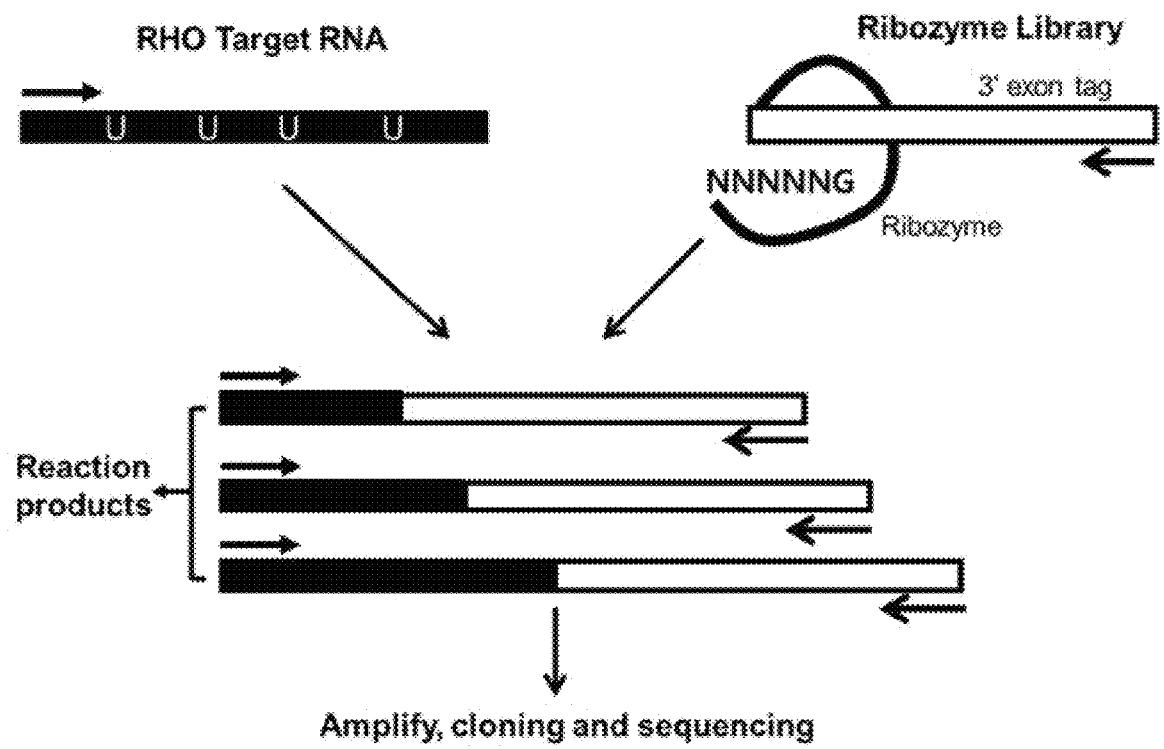

All identified PCR products were subjected to phenol extraction & ethanol precipitation process. After buffer change, a sequencing was performed to determine the site(s) where the trans-splicing reaction occurs in the rhodopsin RNA. Sequencing analysis of trans-splicing reaction sites revealed that most efficient targeting occurred at 59$^{th}$ site that is the 5' UTR region of RHO RNA (FIG. 3A and FIG. 3B).

Intracellular co-transfection was performed by mixing random ribozyme library RNA with rhodopsin RNAs in test tube, to carry out intracellular mapping. Specifically, the 293 cells were seeded in a 35 mm culture dish at a density 1×10$^5$ and were maintained at 37° C. incubator with 5% $CO_2$. The random ribozyme library RNA and rhodopsin RNA were collected in a 1.5 ml tube and mixed with OPTI-MEM™ 100 μl. LIPOFECTAMIN™ 2000 and OPTI-MEM™ 100 μl were added and incubated at room temperature for 5 minutes. Then, the contents of the two tubes were mixed and incubated at room temperature for 20 minutes to allow for liposome complex formation. After 20 minutes, the tubes were centrifuged for 10 seconds and the liposome complex was added on the cells for co-transfection. After 4 hours, the medium was replaced with a new medium. The cells were kept in the incubator at 37° C. with 5% $zCO_2$ for 24 hours. After incubation, the cells were washed with 1×PBS, and RNA was extracted by treatment with trizol 500 ul. 5 μg of the extracted RNA was treated with 1 μl of DNase I to remove gDNA.

1 μg of RNA was mixed with the ribozyme-specific RT primer (5'-ATGTGCTGCAAGGCGATT-3') (SEQ ID NO: 10), and cDNA was synthesized through reverse transcription in a volume condition of 20 μL. 2 μL of synthesized cDNA was amplified with 10 pmol each of rhodopsin RNA specific 5' primer (5' CTACTCAGCCCCAGCGGAGG-3') (SEQ ID NO: 11), ribozyme specific 3' primer (RY-TS) (5'-TGTAAACGACGGCCAGTG-3') (SEQ ID NO: 12) using the following cycling conditions: 35 cycles of 30 sec at 95° C., 30 sec at 55° C., 30 sec at 72° C. PCR products were separated on a 2% TBE agarose gel. PCR products were isolated by phenol extraction & ethanol precipitation. The nucleotide sequence analysis was performed to determine where the trans-splicing reaction occurred within RHO RNA.

Example 3: Preparation of Trans-Splicing Ribozyme

Figure 4:
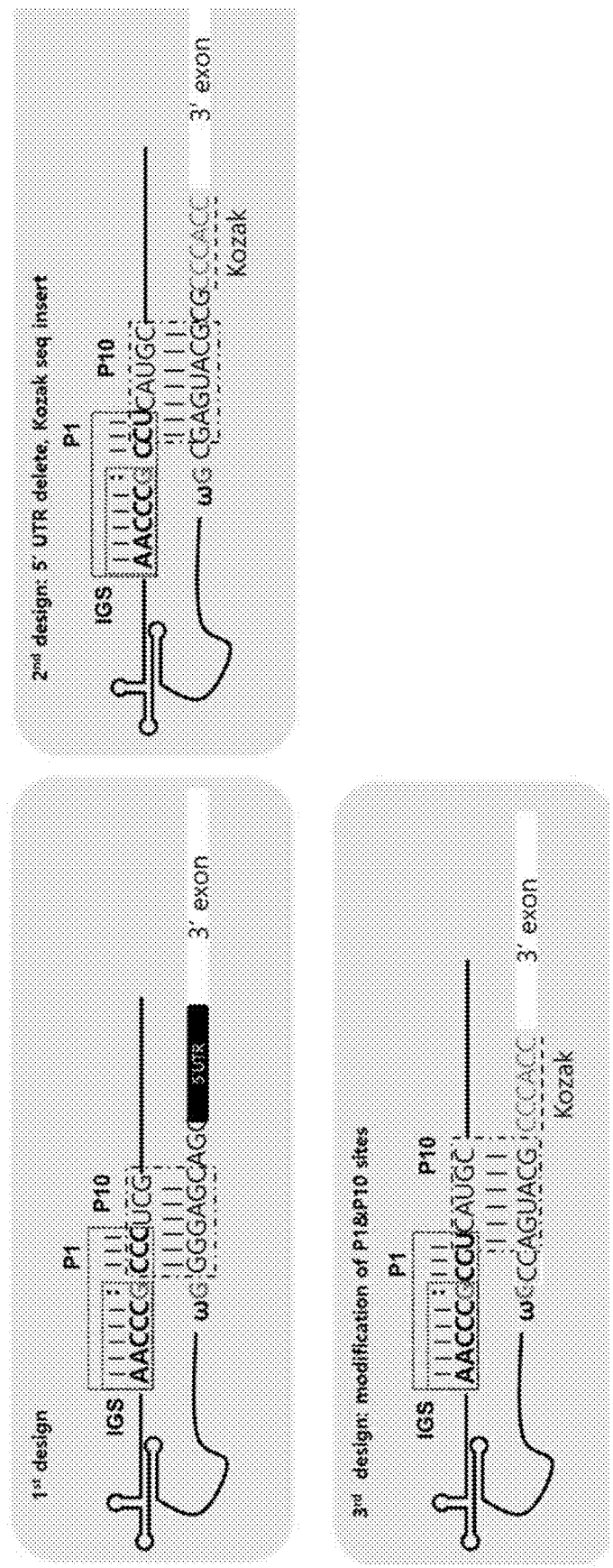
FIG. 4 is a schematic diagram showing optimization of a gene construct comprising a trans-splicing ribozyme according to an embodiment of the present invention targeting +59 site (the base at position 59) of the Rho transcript (hereinafter referred to as "RHO targeting ribozyme").

A gene construct containing a nucleotide encoding normal wild-type rhodopsin ("3' exon' in FIG. 4) and trans-splicing ribozyme targeting the base (U) at position 59 of the RHO transcript (position numbering is based on SEQ ID NO: 1) was manufactured and optimized (FIG. 4). The target region comprises the sequence cagcauucUUGGGUGGGagcagccac (SEQ ID NO: 20) and the target splicing site is U at position 59 (underlined) of RHO RNA, and the construct includes IGS (5'-GCCCAA-3': SEQ ID NO: 18), at the 5' end, wherein the IGS is capable of partially complementarily binding to the above target region. To analyze the trans-splicing efficiency of the ribozyme targeting RHO RNA +59 base ("RHO target ribozyme") in cells, an improved RHO targeting ribozyme construct was prepared. It is known that Group I introns having 6-nt IGS alone are, when expressed in mammalian cells, either inactivated or exhibit non-specific activity.

To prepare an improved RHO targeting ribozyme construct, a complementary oligonucleotide containing an extended P1 (5'-CCCGCCCAA-3' (SEQ ID NO: 14) and/or 5'-UCCGCCCAA-3' (SEQ ID NO: 21)) and 7-nt long P10 helix (5'-CGUACUC-3' (SEQ ID NO: 15) and/or 5'-GAGUACG-3' (SEQ ID NO: 16)) was inserted to the upstream of IGS of the ribozyme.

Example 4: Optimization of Trans-Splicing Ribozymes

Figure 5:
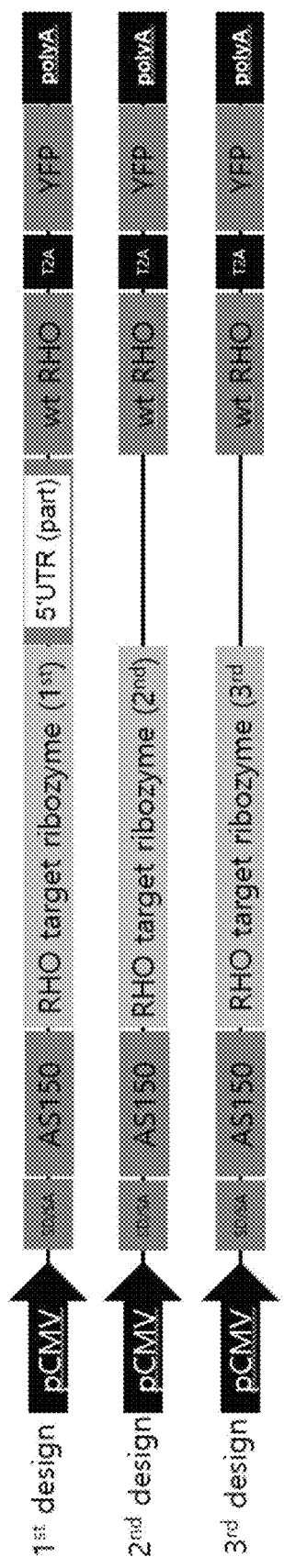
FIG. 5 is a schematic diagram of a vector including a RHO targeting ribozyme according to an embodiment of the present invention.

To confirm that RHO targeting ribozyme was optimized for trans-splicing, vectors were constructed with RHO targeting ribozyme of the first, second and third design prepared in Example 3 (FIG. 5).

In FIG. 5, AS150 is SEQ ID NO: 6; SD/SA is SEQ ID NO: 7; sequence of part of 5'UTR is SEQ ID NO: 8. Linker sequence T2A, YFP and polyA sequences are well known in the art and their specific nucleotide sequences are omitted.

Figure 6D:
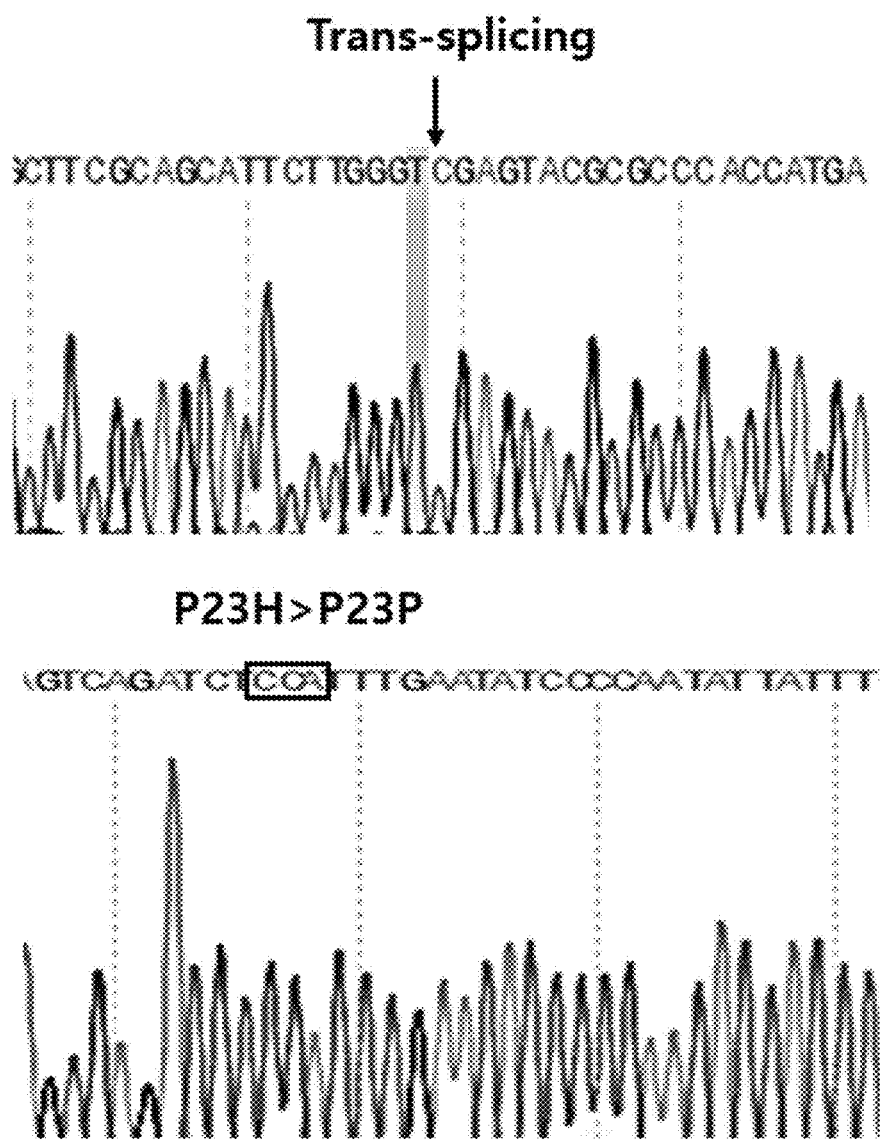

The effect of the three designs of RHO targeting ribozyme was investigated. Comparative verification was performed in vitro (in mammalian cells). The results are shown in FIG. 5. Design 1 was compared to design 2 and it was confirmed that the trans-splicing efficiency of design 2 was better (FIG. 6A). Comparison of designs 2 and 3 demonstrated that the trans-splicing efficiency of design 2 was better (FIG. 6B). Antisense sequences of different lengths were compared to optimize the specificity and effectiveness of the ribozyme. Antisense sequence of 150 nucleotides in length (SEQ ID NO: 6) was found to be the most effective (FIG. 6C). Sequencing of trans-splicing products was performed to confirm that trans-splicing was performed accurately. It was confirmed that trans-splicing occurred at the target site (FIG. 6D).

Example 5: Assay for Trans-Splicing Activity In Vitro

The in vitro efficacy of RHO-targeting ribozyme was confirmed using stable cells. A YFP-tagged wild-type RHO (wild Rho-YFP) was used as a positive control. A 293A cell line stably expressing WT or P23H RHO was prepared, and functional analysis was performed in this cell line. Normal rhodopsin proteins migrate to and localizes at the cell membrane. However, rhodopsin with P23H mutation does not fold properly and does not localize at the cell membrane but stays in the endoplasmic reticulum. Therefore, by identifying the location of the protein, the functional change of the protein can be confirmed.

The RHO targeting ribozyme expression vector was transfected into stable cells. To confirm the trans-splicing effect, RNA was extracted, and RT-PCR was carried out.

Specifically, 1×10$^5$ stable cells were seeded in a 35 mm culture dish and grown in an incubator at 37° C. with 5% $CO_2$. 2 μg of RHO-targeting ribozyme expression vector and 100 μl of OPTI-MEM™ were mixed in a 1.5 ml tube. 2 μl of LIPOFECTAMINE® 2000 and 100 μl of OPTI-MEM™ were mixed in another 1.5 ml tube and incubated at room temperature for 5 minutes. After that, the contents of the tubes were combined and mixed and incubated at room temperature for 20 minutes to allow the formation of a liposome complex. After 20 min, the tube was centrifuged for 10 sec. The mixture was added to plated cells for transfection and incubated for 4 hours, after which the transfection medium was replaced with fresh medium.

The cells were then placed in an incubator for 48 hours at 37° C. with 5% $CO_2$. After 48 hours, the cells were washed with 1×PBS and RNA was extracted with 500 µl of trizol. 5 µg of extracted RNA was treated with 1 µl of DNase I to remove gDNA. 1 µg of treated RNA was reverse transcribed to obtain cDNA. Using the synthesized cDNA, the trans-splicing product was amplified by PCR and purified. It was confirmed that the trans-splicing action occurred at the target site by nucleotide sequence analysis (FIG. 7A).

In addition, after transfection of the RHO targeting ribozyme expression vector as described above, the cells were stained using an anti-RHO antibody and a secondary fluorescently labeled antibody. The intracellular distribution of RHO protein was analyzed by a fluorescence microscopy. It was confirmed that in the cells transfected with the RHO targeting ribozyme, RHO proteins were localized to the cell membrane, whereas the RHO proteins with P23H mutation were dispersed in cytosol (FIG. 7B).

Figure 8:
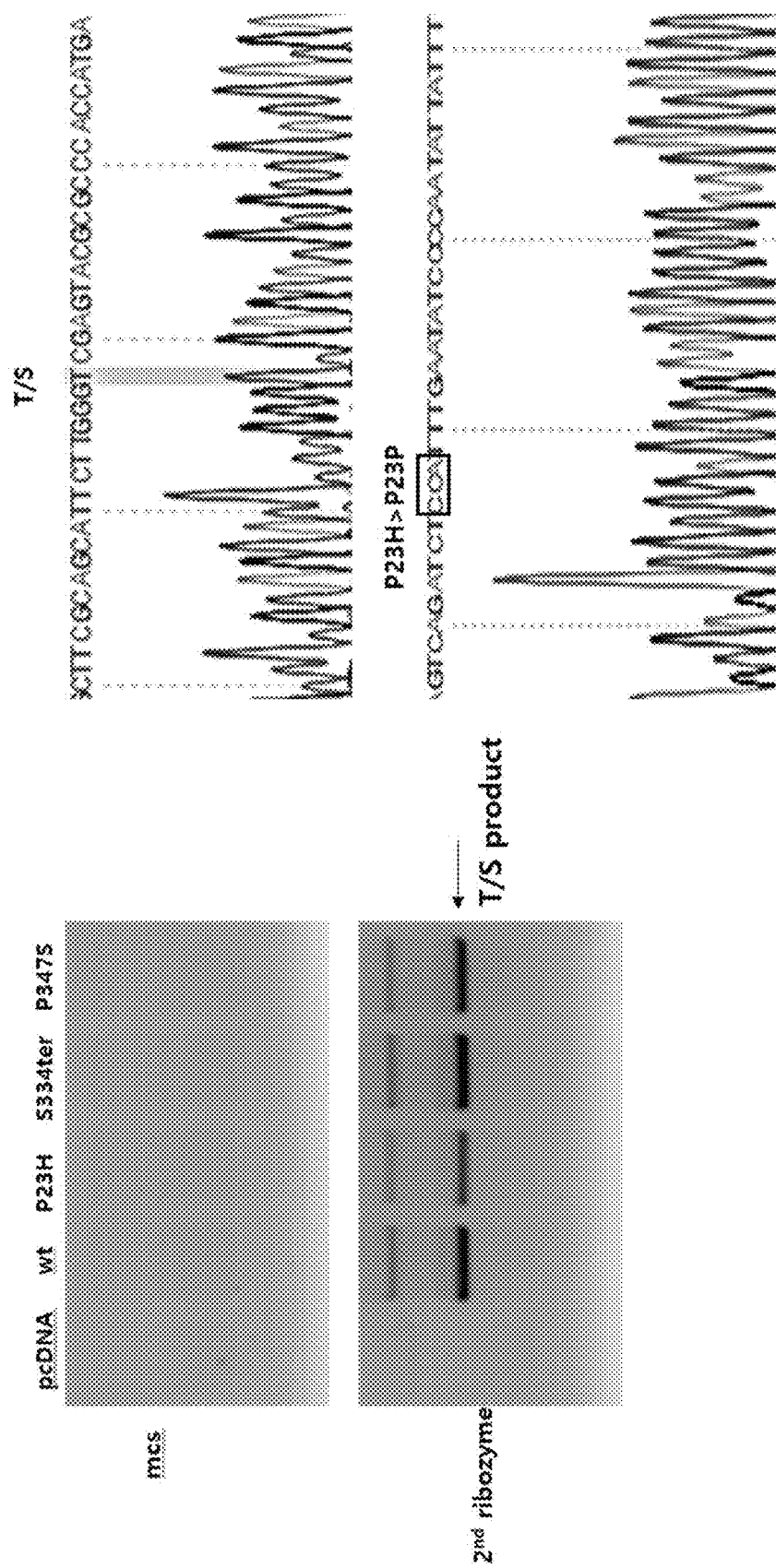
FIG. 8 shows the results of an experiment confirming in vitro efficacy of RHO-targeting ribozymes against various RHO mutations.

In addition, in vitro efficacy of RHO targeting ribozymes specific for various mutations was demonstrated in 293A cells by co-transfection (FIG. 8). Specifically, 0.5 µg of the RHO-targeting ribozyme expression vector and 2 µg of expression vectors with various RHO mutant transcripts were mixed with 100 µl of OPTI-MEM™ in a 1.5 ml tube. 2.5 µl of LIPOFECTAMIN™ 2000 and 100 µl of OPTI-MEM™ were mixed in another 1.5 ml tube and incubated at room temperature for 5 minutes. Cell transfection and RT-PCR were performed as described above. It was confirmed that mutant RHO transcripts were successfully replaced with normal RHO RNA by RHO-targeting ribozymes. Therefore, a trans-splicing ribozyme according to embodiments of the present disclosure can correct a specific RHO mutation by replacing the mutation site with WT sequence regardless of the type of mutation.

Figure 9:
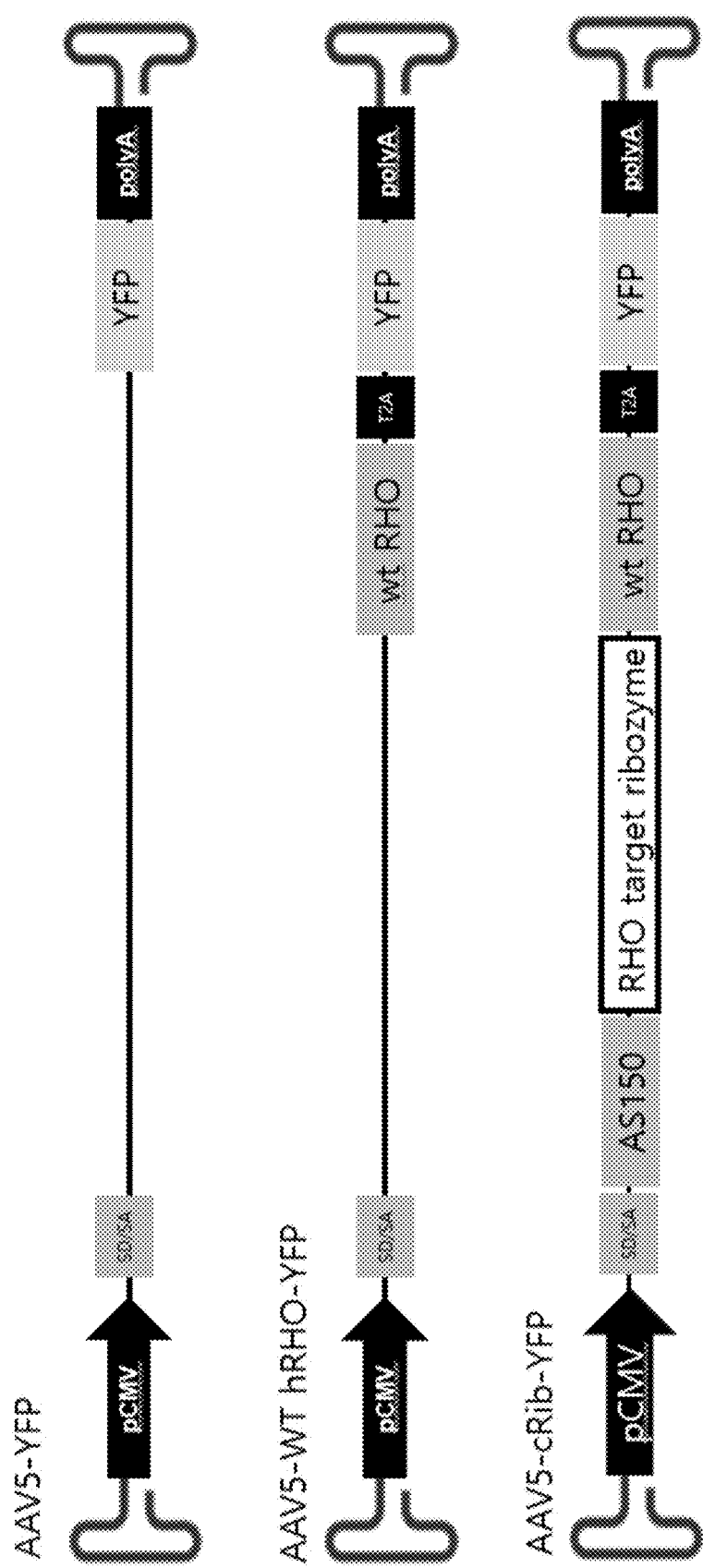
FIG. 9 is a schematic diagram of a recombinant AAV expression vector comprising a RHO targeting ribozyme according to an embodiment of the present invention.

Example 6. Recombinant Virus Construction and Confirmation of Trans-Splice Efficacy in Animal Models of RHO-adRP 6-1: Recombinant Virus Construction An expression vector was constructed using an Adeno-associated viruses (AAV) vector as a backbone, a RHO-targeting ribozyme of the second design of Example 4, and a CMV promoter (FIG. 9). 20 µg of the backbone pAAV plasmid was digested with EcoRI and eluted on an agarose gel. After reacting DNA construct containing ribozyme with WT RHO synthesized using an IN-FUSION® HD cloning kit, transformed colonies were obtained. Each colony was cultured, plasmid was isolated and sequenced, and then clones with the correct cloned sequence were selected. The isolated plasmid was digested with EcoRV and XbaI, separated on the agarose gel and eluted. Synthesized YFP DNA was inserted using an IN-FUSION® HD cloning kit. Bacteria were transformed with the resulting construct. Plasmids were extracted from resulting colonies and correct cloning was confirmed by sequencing. In order to add the antisense sequence, selected constructs were digested with EcoRI, separated on an agarose gel and eluted. The AS150 sequence obtained by PCR is reacted using an IN-FUSION® HD cloning kit to obtain colonies. After sequencing the colonies in the same way, the final AAV-cRib-YFP plasmid was obtained.

HEK-293T cells were triple transfected with the Helper vector, RHO ribozyme expression vector and Rep2Cap5 vector to produce an AAV viral vector. The transfected cells were lysed 72 hours post-transfection and supernatant was harvested using PEG precipitation. AAV viral vector was purified by density gradient ultracentrifugation using iodixanol.

6-2: Confirmation of the Efficacy of Trans-Splicing Ribozymes in Animal Models of RHO-adRP The efficacy of ribozyme was confirmed in hP23H-RFP mouse model of RHO-adRP using the AAV expression vector of Example 6-1. hP23H mouse-RFP mouse model is a knocked-in model carrying an RFP-tagged human P23H RHO. It is a model widely used in RHO P23H studies. 1 µl of AAV expression vector was injected into the subretinal space of each mouse eye. The injection was performed using the IO kit with 34G needle and 1 µl of the vector was injected per eye into both eyes by scleral puncture. Upon completion of administration, antibiotics were injected into the eyes of the mouse and eye drops were used to prevent infection. The success or failure of administration was determined by confirming the formation of a bleb by FP/OCT imaging.

Figure 10A:
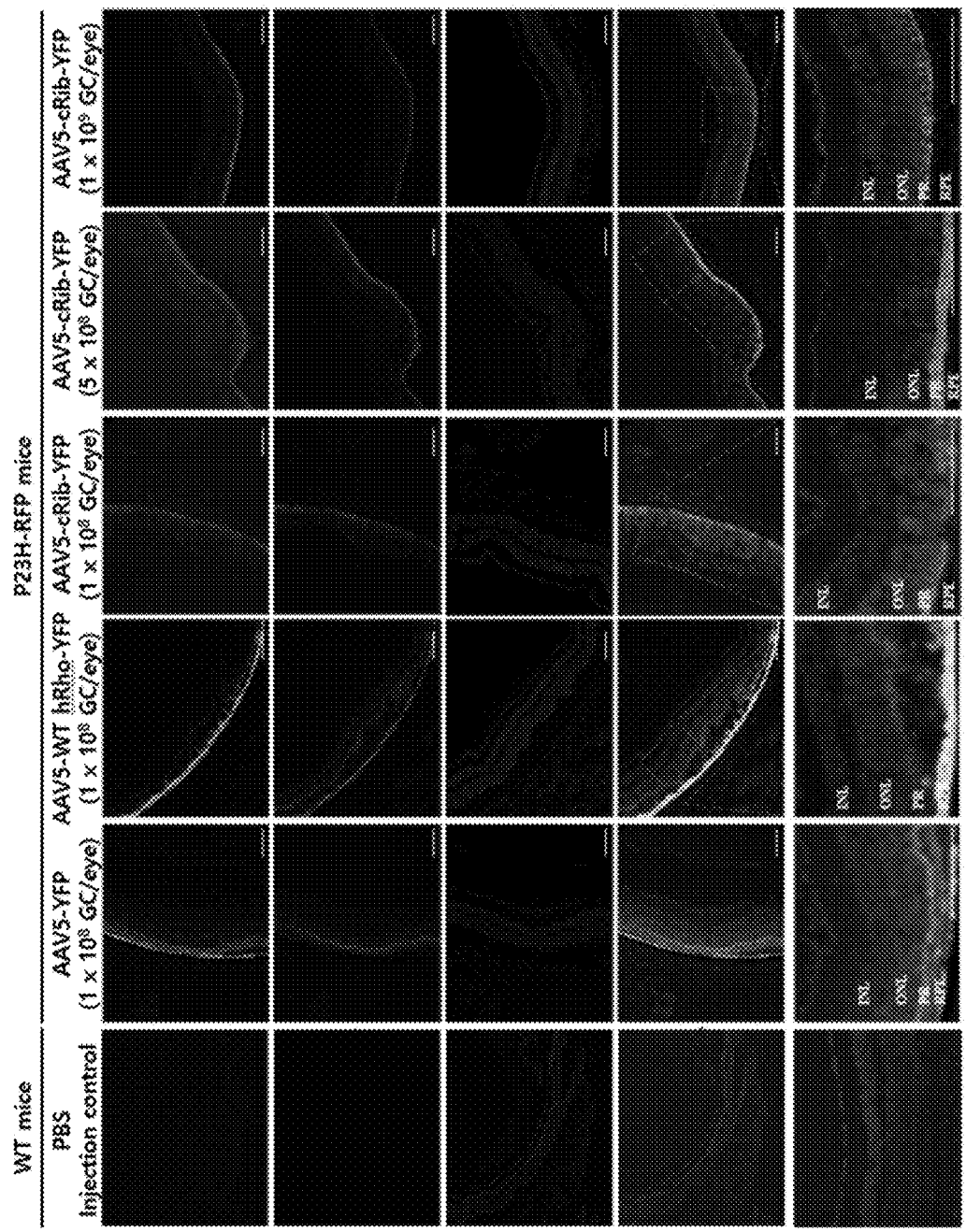
FIG. 10A and FIG. 10B are microscopic photos of the eyeballs of hP23H-RFP ADRP mouse model, in which cells of the eyeballs were stained with DAPI. The photos confirm the efficacy of ribozyme in a mouse model using an AAV expression vector comprising a RHO targeting ribozyme according to an embodiment of the present invention.
Figure 10B:
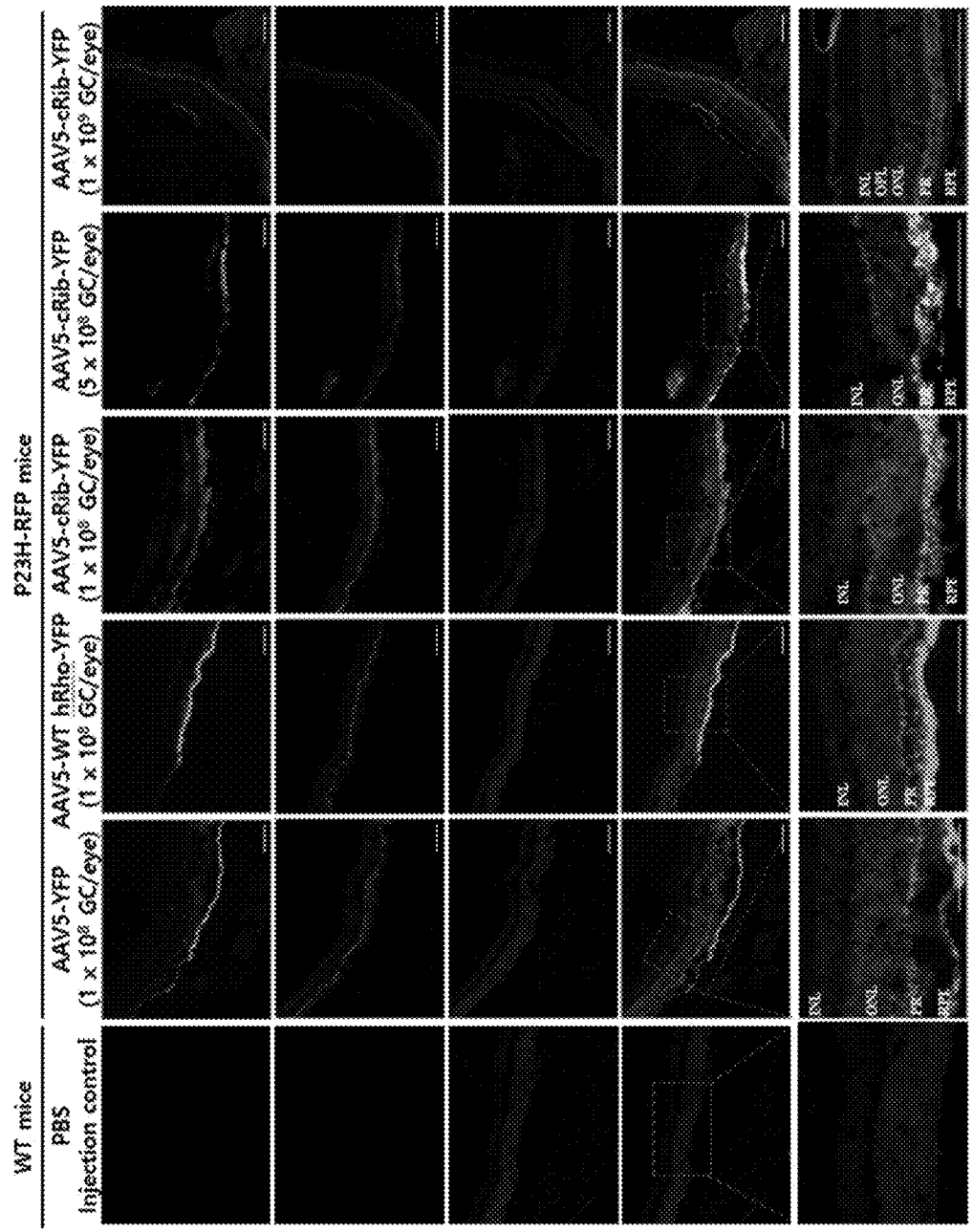

At 2 or 5 weeks after administration, the eyeballs were removed, and tissue section slides were prepared. Cell nuclei were stained by DAPI. Staining of RHO protein itself was not performed because RHO was labeled with YFP. FIG. 10 shows the results of 2 weeks after administration (FIG. 10A) and 5 weeks after administration (FIG. 10B).

AAV5-YFP (fluorescence positive) and AAV-WT hRho-YFP (gene, fluorescence positive) were used as a control for AAV5-cRib-YFP. Fluorescence of AAV5-YFP and AAV-WT hRho-YFP were observed also in retinal pigment epithelium (RPE), indicating that these were not introduced in a photoreceptor specific manner. On the other hand, in the case of AAV5-cRib-YFP carrying the RHO targeting ribozyme, no expression was observed in RPE and its expression was observed in photoreceptors only.

Figure 11A:
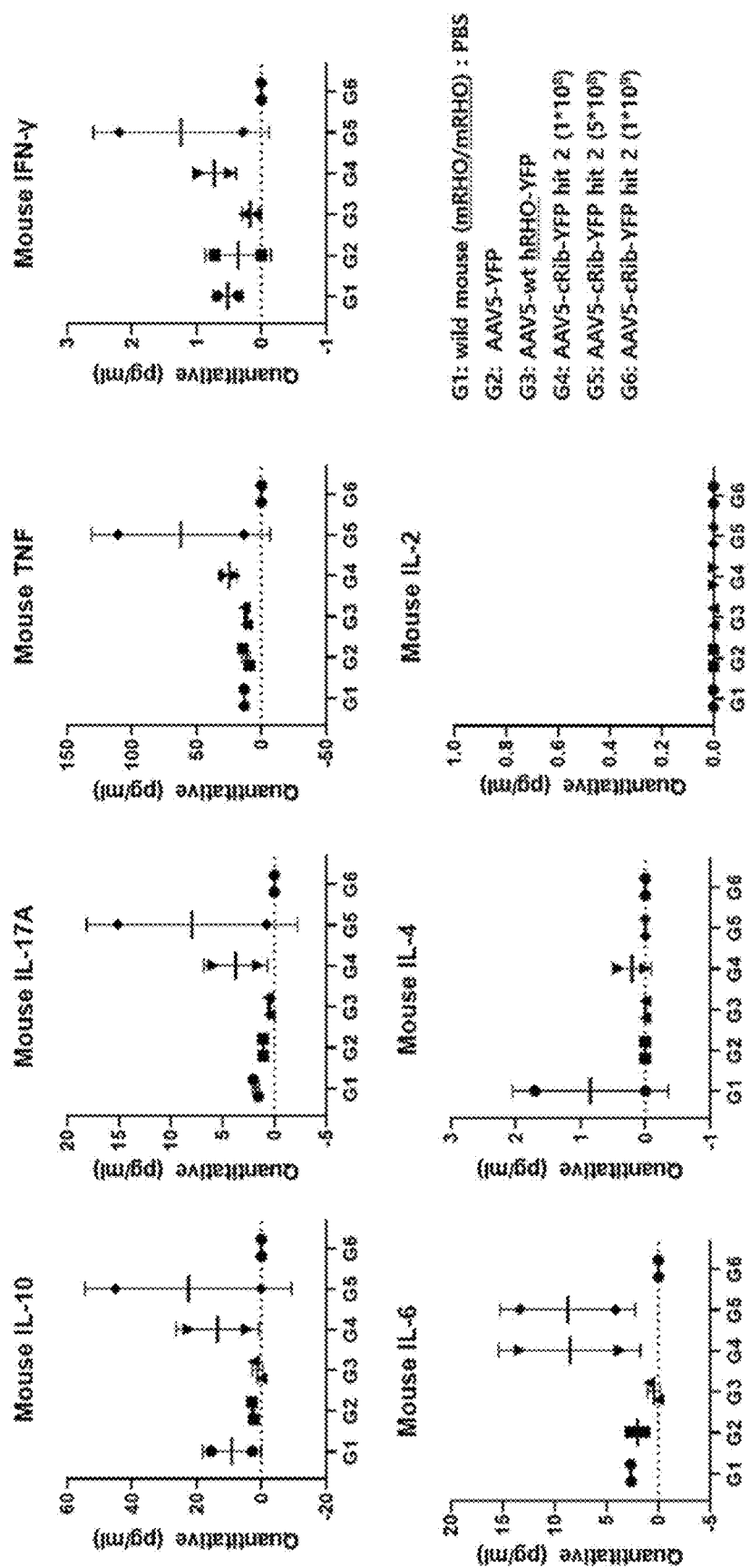
FIG. 11A and FIG. 11B show immune and inflammatory responses in serum after administration of an AAV vector containing RHO targeting ribozyme in an hP23H-RFP ADRP mouse model according to an embodiment of the present invention.
Figure 11B:
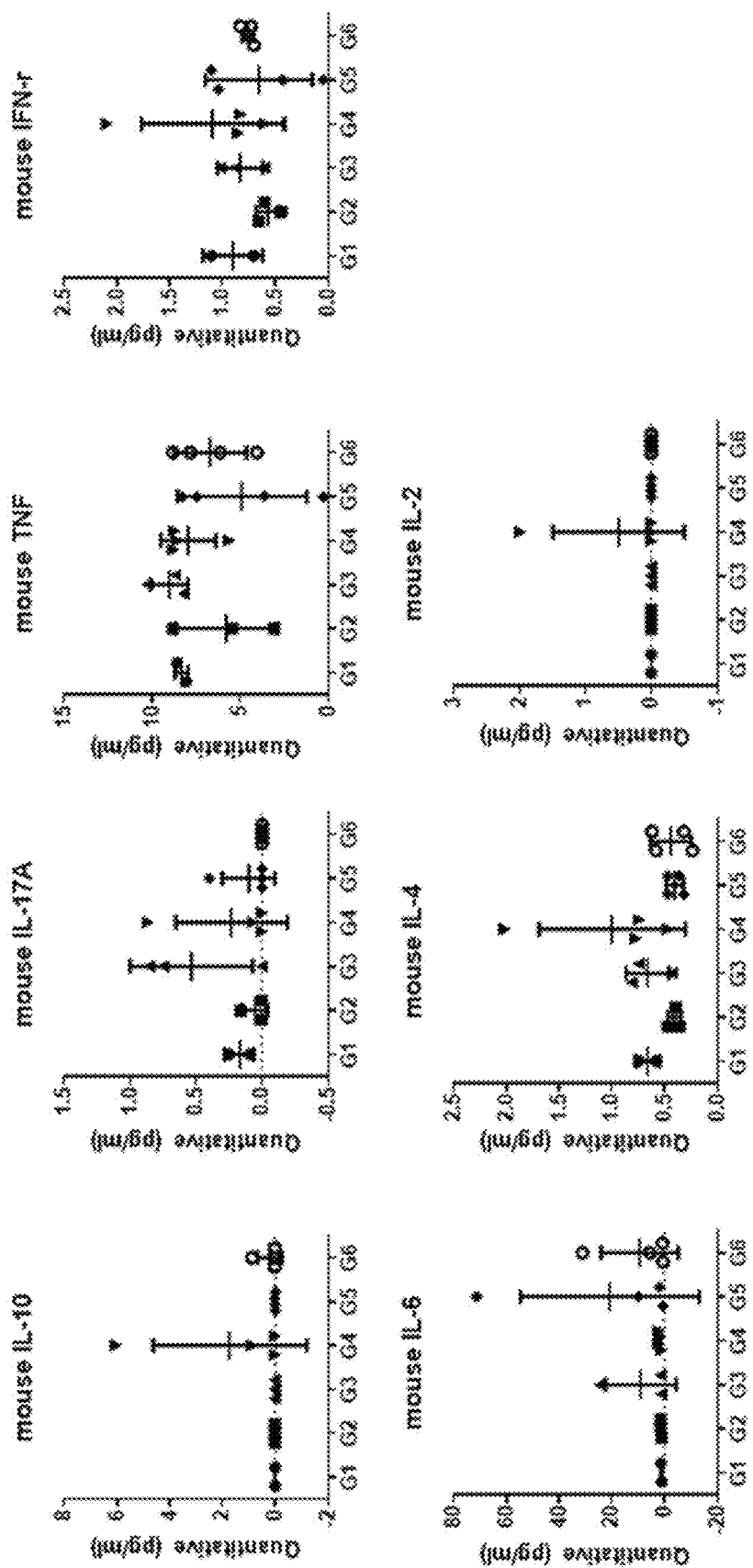

Example 7: Assessment of Immune Reaction and Inflammatory Reaction after Administration of Trans-Splicing Ribozyme in Animal Model of RHO-adRP The results of assessing the immune and inflammatory responses in the serum of hP23H-RFP mice after administration of a trans-splicing ribozyme are shown in FIG. 11 (FIG. 11A: 2 weeks after administration; FIG. 11B: 5 weeks after administration).

An increase in IL-6, IL-17A, TNF-α, INF-γ, and IL-10 levels was observed at 2 weeks after AAV5-cRibYFP administration, and no changes in IL-4 and IL-2 levels were observed. Such changes were not observed in the AAV5-YFP and AAV-WT hRho-YFP-treated control groups, indicating that these changes are not attributed to viral vectors. Cytokines, which were increased at 2 weeks, returned (decreased) to levels of the control groups at the 5 weeks, indicating that inflammation and immune response are increased at the early subretinal administration and then returned to the original level at 5 weeks.

Example 8: Confirmation of Activity of Ribozyme in Retina and Retinal Pigment Epithelium (RPE) Tissue in an Animal Model of RHO-adRP after Administration of Trans-Splicing Ribozyme Occurrence of trans-splicing reaction through targeting RHO RNA in the photoreceptor was confirmed in the animal model after administration of a trans-splicing ribozyme. For this, the mouse eyeball was removed, retina and retinal pigment epithelial cells (RPE/choroid) were isolated, RNA was extracted and RT-PCR was performed to observe and confirm the production of trans-splicing products. The results are shown in FIG. 12.

Figure 12A:
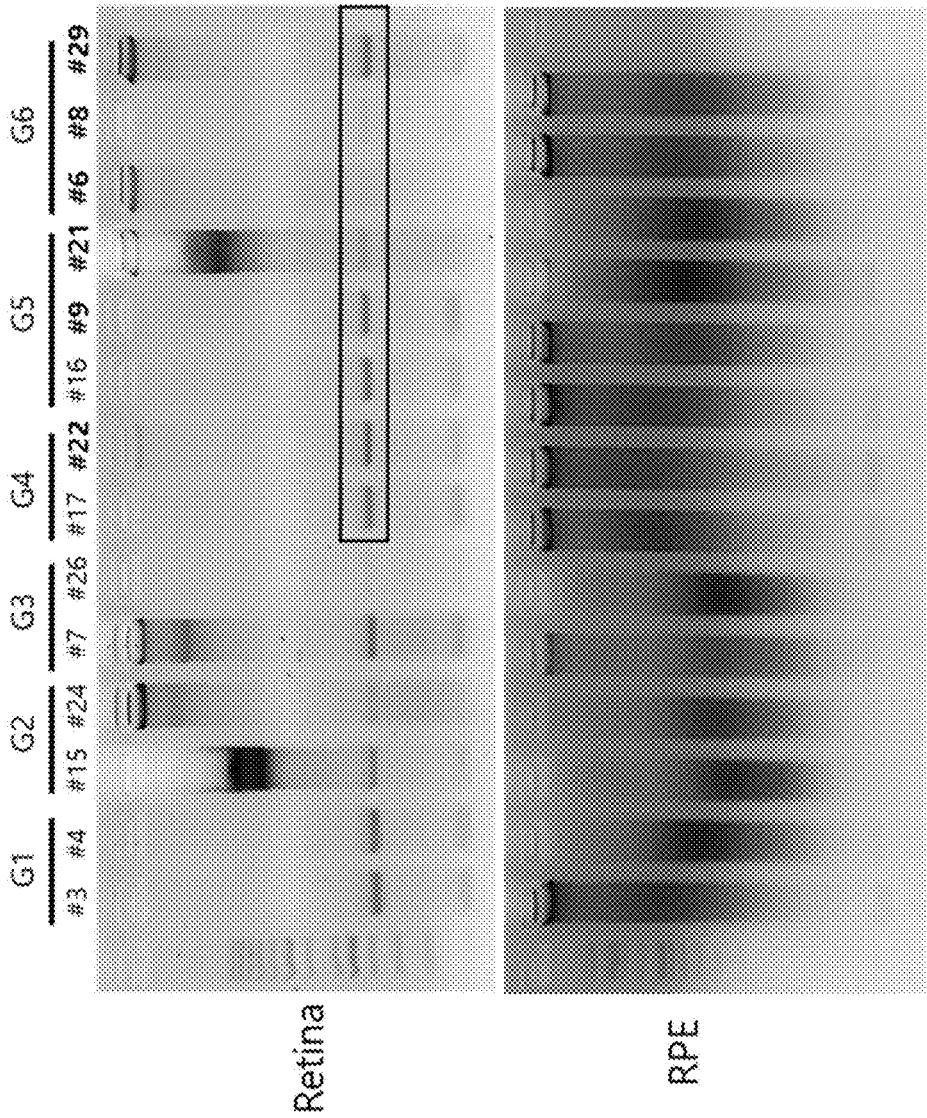
FIG. 12A-FIG. 12C show experimental results confirming the efficacy of the RHO targeting ribozyme in retina and retinal pigment epithelium (RPE) in a hP23H-RFP ADRP mouse model after administration of the AAV vector according to an embodiment of the present invention.
Figure 12B:
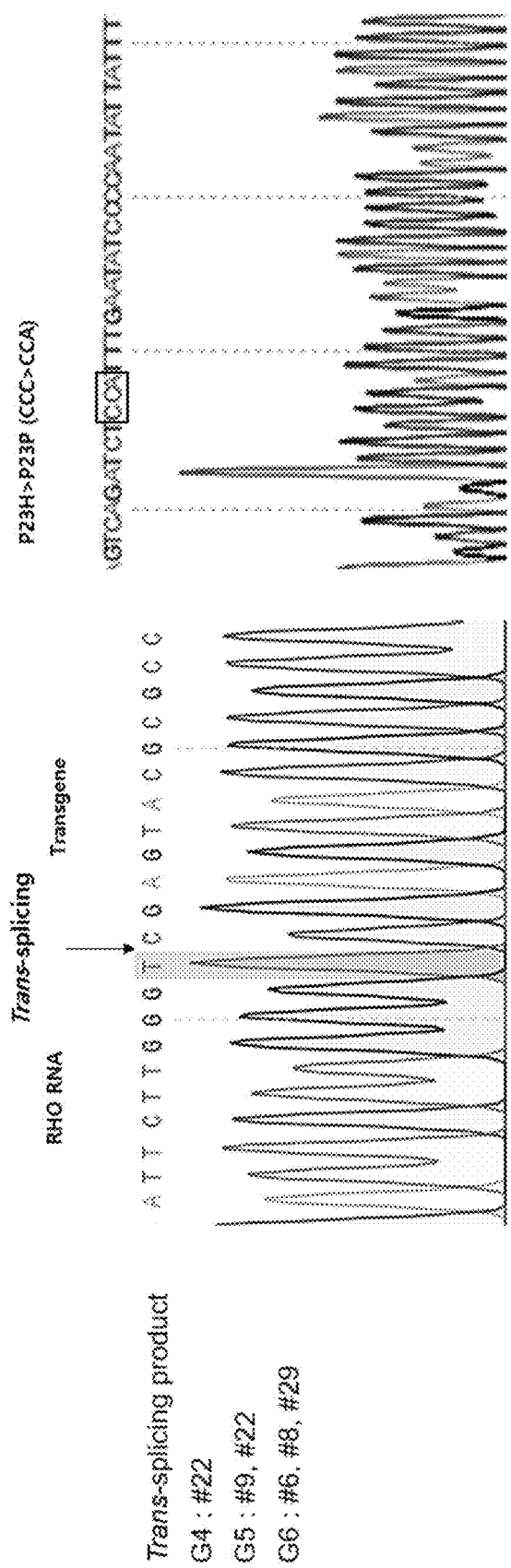
Figure 12C:
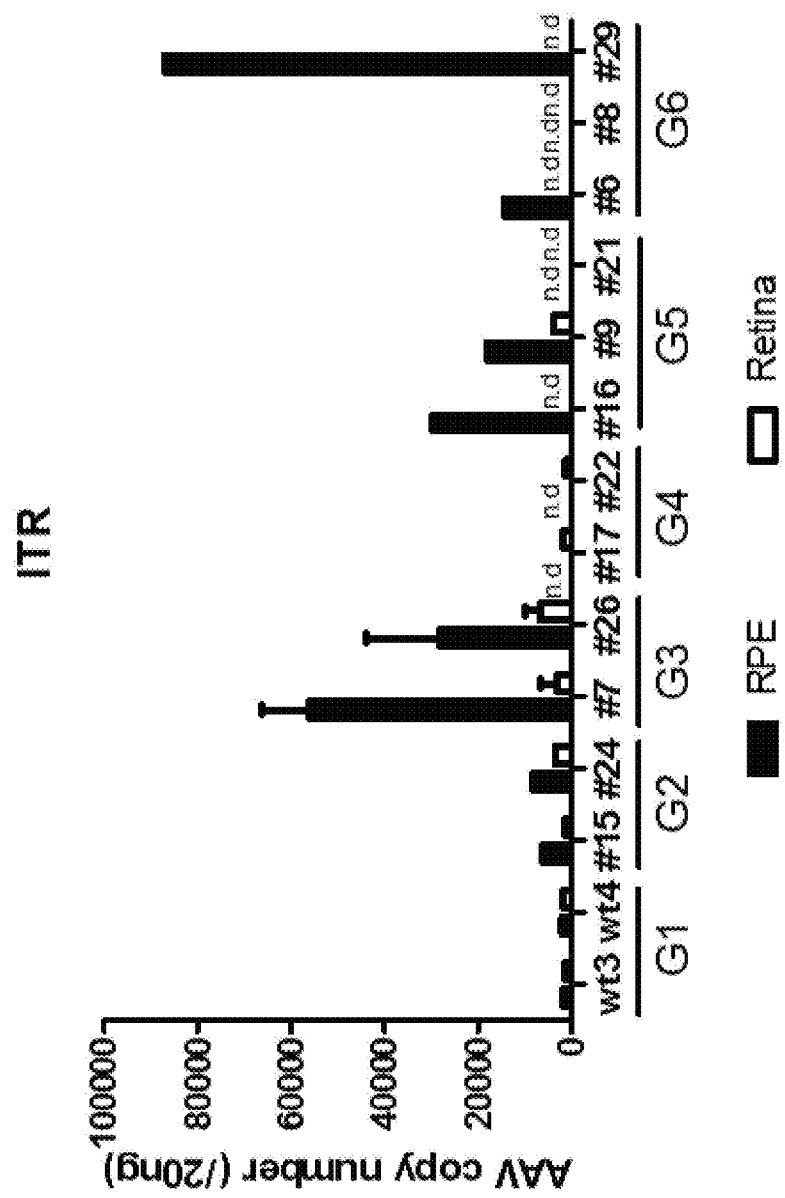

The amplified trans-splicing product PCR band could not be identified in a sample extracted from RPE. Retina-specific trans-splicing products were identified (FIG. 12A). Sequencing was performed on the amplified trans-splicing product to confirm that the mutant RHO RNA was targeted and substituted with normal RHO RNA (FIG. 12B).

In addition, when the AAV ITR region was amplified after extracting gDNA from the retina and retinal pigment epithelial (RPE) cells, higher levels were detected in retinal pigment epithelial cells than in the retina (FIG. 12C), which indicates that AAV vectors are well delivered to RPE. However, transgene expression controlled by ribozyme was photoreceptor-specific.

Figure 13:
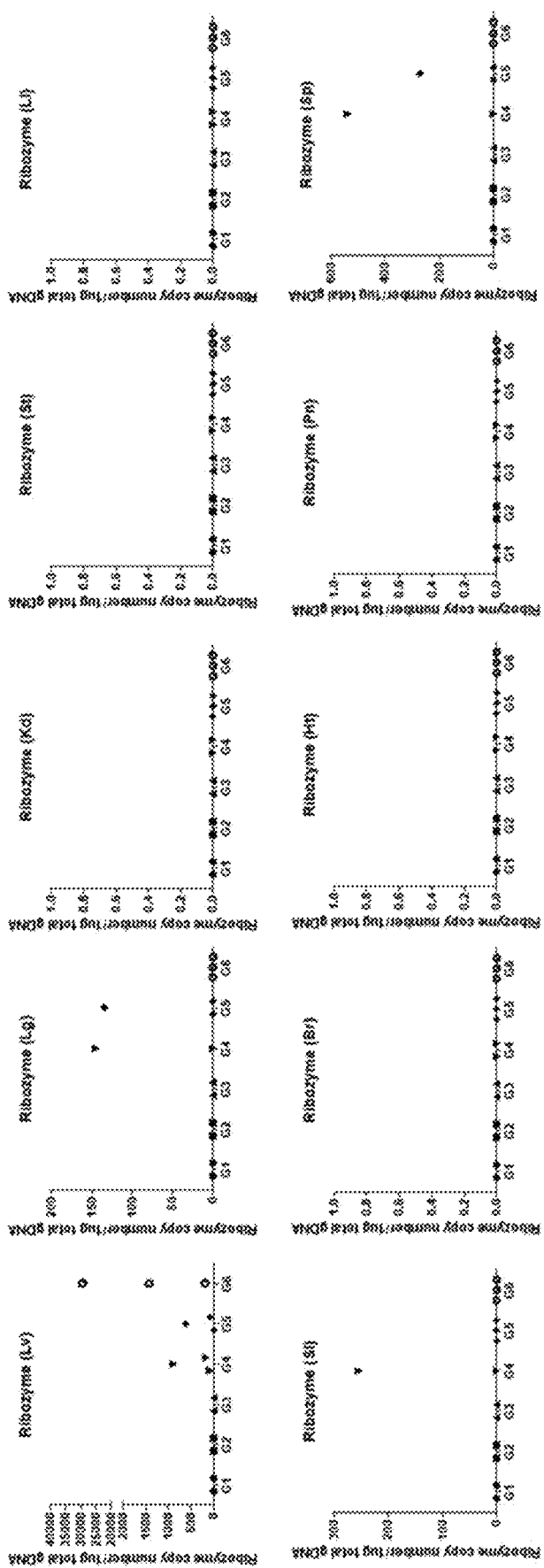
FIG. 13 shows the in vivo distribution of RHO target ribozyme in a hP23H-RFP ADRP mouse model after administration of an AAV vector comprising the ribozyme according to an embodiment of the present invention.

Example 9: Distribution of Ribozymes In Vivo after Administration of Trans-Splicing Ribozyme in Mouse Model of RHO-adRP 2 weeks after administration of ribozyme to hP23H-RFP mice, the distribution of ribozymes in organs was confirmed (FIG. 13). The mice were sacrificed at 2 weeks after administration, whole organs were obtained, and gDNA was isolated and purified. Real-time PCR was performed using 1 μg of gDNA from each organ with a ribozyme-specific primer. Ribozymes were detected within a detection range in the liver of all animals administered with the trans-splicing ribozyme expression vector. In some animals, ribozymes were detected within a detection range in the lung, small intestine, and prostate. Ribozymes were not detected in other organs and tissues.

Figure 14:
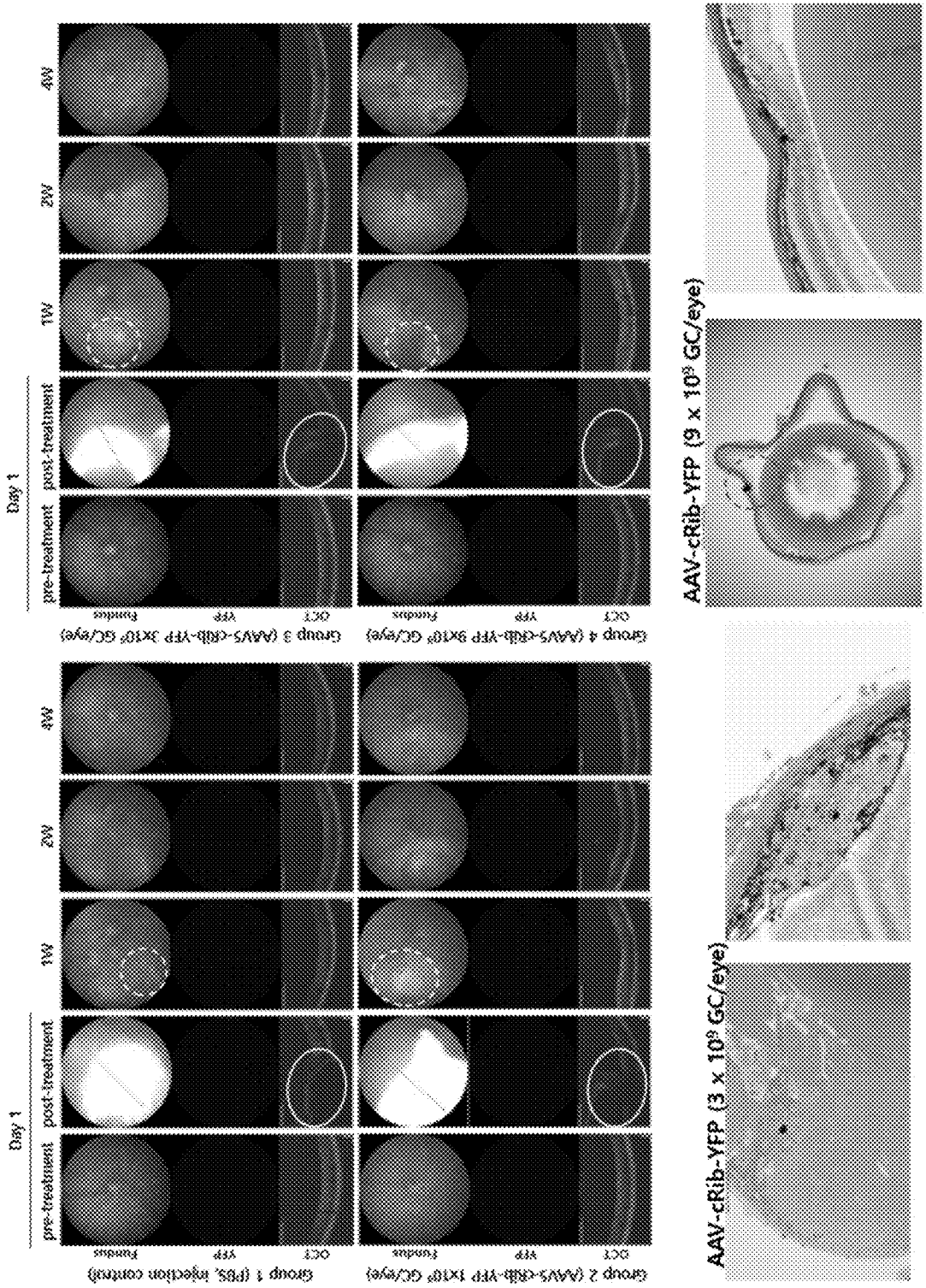
FIG. 14 is microscopic photos of H&E stained eyes of normal mice, showing the result of analyzing the toxicity after administration of the AAV vector containing a RHO targeting ribozyme in a normal mouse according to an embodiment of the present invention.

Example 10: Toxicity Analysis after Administration of Trans-Splicing Ribozyme to Normal Mice Toxicity after administration of trans-splicing ribozymes was assessed in normal mice (C57BL/6J). Images of fundus and OCT images were taken each week for 4 weeks after administration, and H&E staining was performed (FIG. 14). It was confirmed that the bleb formed in the test group at the site of subretinal administration (solid line in FIG. 14). Corneal inflammation and vitreous bleeding occurred in some individuals (dotted line). Lens degeneration, retinal degeneration and outer retina were observed in the groups treated with $3 \times 10^9$ GC/eye by H&E staining. The occurrence of atrophy and histological inflammation of the choroid was also observed. No toxicity was observed at the concentration of less than $1 \times 10^9$ GC/eye.

Figure 15:
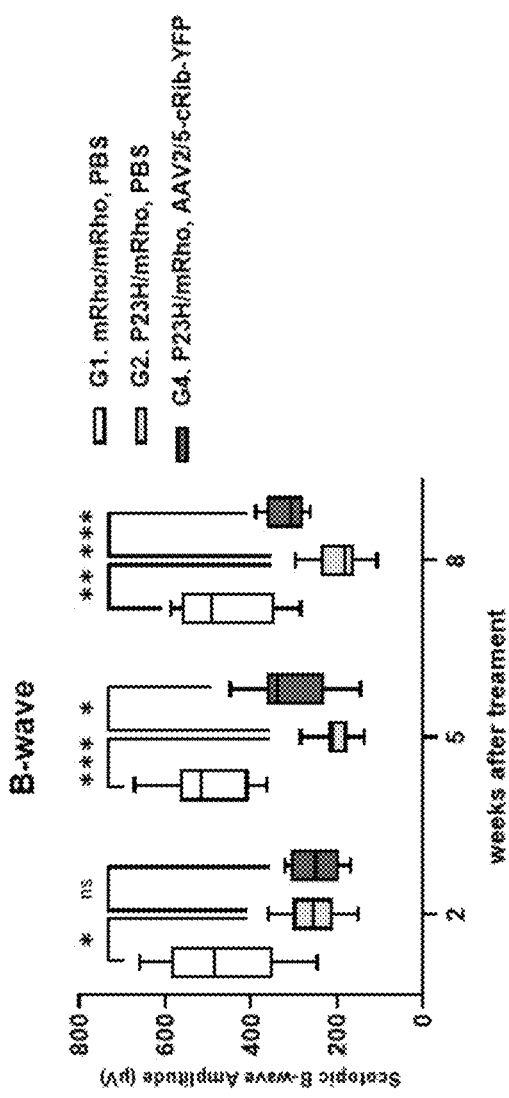
FIG. 15 shows the result of performing an electroretinogram test after administration of the AAV vector containing a RHO targeting ribozyme in a hP23H-RFP ADRP mouse model according to an embodiment of the present invention.

Example 11: Electroretinogram after Administration of Trans-Splicing Ribozyme in Mouse Model of RHO-adRP Electroretinogram (ERG) was performed at indicated time intervals after administration of trans-splicing ribozyme in 5 weeks-old hP23H-RFP mice (FIG. 15 and Table 1). Scotopic-ERG responses were evaluated and amplitude of B-wave were compared. Mice were anesthetized with ketamine for electroretinogram evaluation. After additional local anesthesia, pupils of eye were dilated with eye drops. Mice were placed on the stage and electrodes were placed on the tail end, glabella, and retina, and ERG responses were recorded simultaneously from both eyes. Full-filed ERG were recorded at a flash intensity of 0.9 log cds/m² (10 responses/intensity). After the measurement was complete, one drop of antibiotic ophthalmic solution was administered into the mouse eye. 'LabScribeERG (iWorx DataAcquisition Software)' program was used for the analysis.

The P23H mutation of the rhodopsin leads to loss of normal function and visional impairment by inducing the death of rod cells and cone cells. It impairs the ability of retire photoreceptor cells (rods and cones) to convert light energy into electrical signals. As the number and function of photoreceptor cells decreases, the electrical signals diminish. The evaluation of these electrical signals was performed through electroretinography (ERG) to assess the difference in visual function. In electroretinography, B-wave is an indicator that determines whether an electrical signal is transmitted. B-wave was significantly increased at 5 weeks after administration of RHO-targeting ribozyme (AAV5-cRib-YFP) and this effect persisted until 8 weeks. Thus, maintenance and improvement of visual function was observed in disease models treated with AAV5-cRib-YFP.

TABLE 1

| Scotopic B-wave Amplitude (μV) | C57BL/6J PBS treatment | P23H-RFP (+/−), PBS treatment | P23H-RFP (+/−), AAV5-cRib-YFP treatment |
| --- | --- | --- | --- |
| Week 2 after administration | 471.6 ± 139.12 | 258.2 ± 62.68 | 251.1 ± 56.08 |
| Week 5 after administration | 500.5 ± 101.22 | 204.7 ± 39.73 | 308.1 ± 92.87 |
| Week 8 after administration | 462.7 ± 116.38 | 193.6 ± 55.66 | 318.6 ± 46.17 |

Figure 16A:
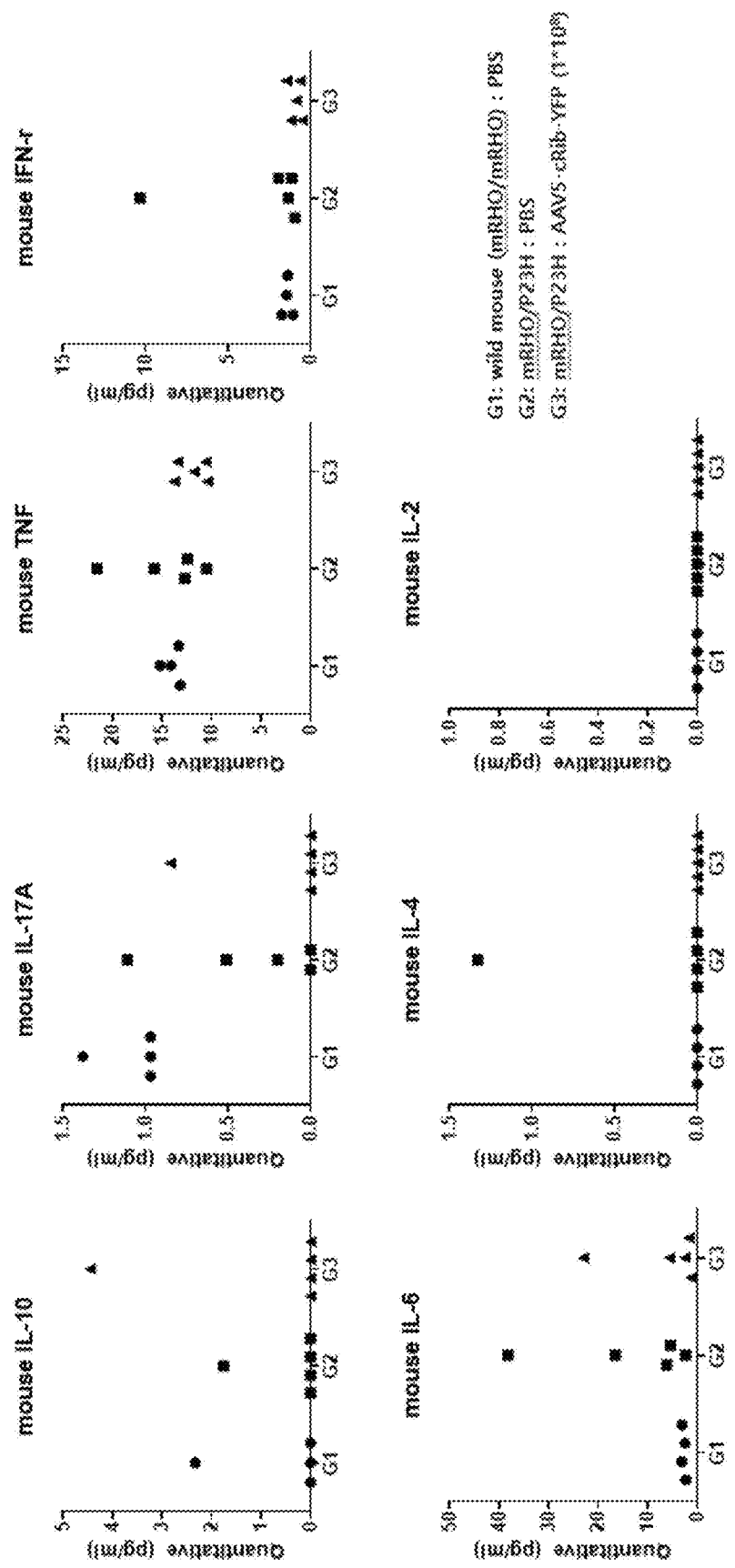
FIG. 16A shows the results of the analysis of serum and FIG. 16B shows the results of ribozyme activity, after administration of the AAV vector containing a RHO targeting ribozyme according to an embodiment of the present invention in a hP23H-RFP ADRP mouse model.

Example 12: Analysis of Ribozyme Activity and Serum after Administration of Trans-Splicing Ribozyme in Mouse Model of RHO-adRP Serum analysis and ribozyme activity analysis were performed at 8 weeks after administration of trans-splicing ribozyme in hP23H-RFP mice (5 weeks old) (FIG. 16). At week 8, when comparing normal animals (G1) administered with PBS and the animal model (G2) group administered only with PBS, no change in cytokines was observed by administration of trans-splicing ribozyme (FIG. 16A). In Example 7, cytokine changes were observed at week 2 and then returned to a same level as normal control group animals at week 5. Thus, the results in this Example and results of Example 7 mean that the administration of the trans-splicing ribozyme does not affect cytokine changes even at week 8.

Figure 16B:
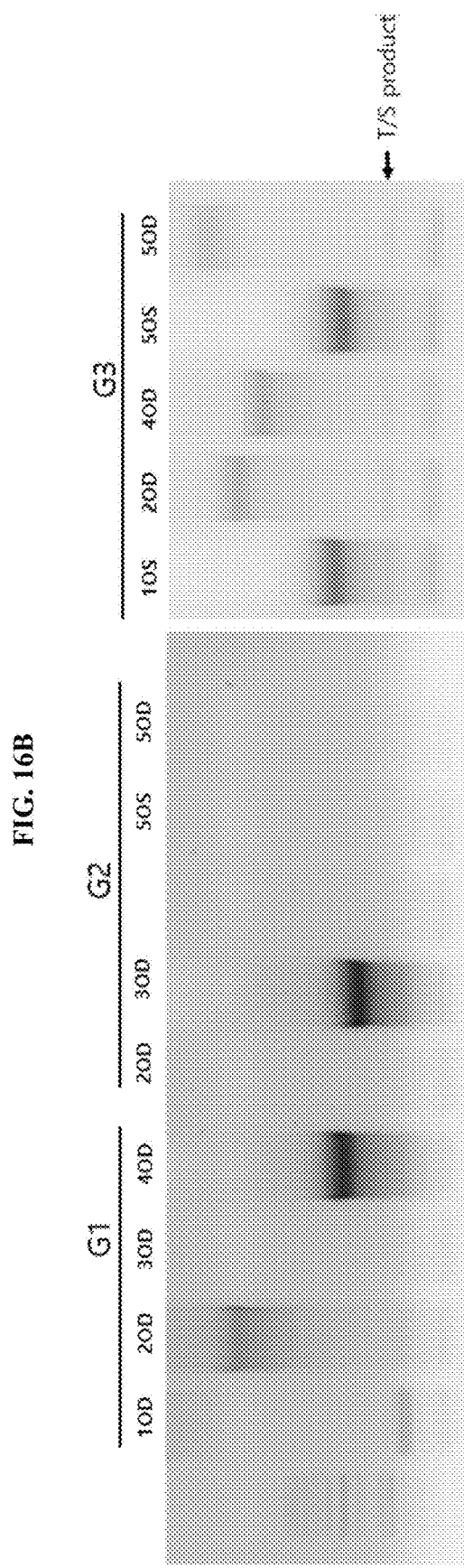

To assess whether or not RHO RNA-targeting trans-splicing action is maintained at week 8, RNA was extracted from the retina of the mice and presence of trans-splicing products was confirmed by RT-PCR (FIG. 16B). The expression and action of AAV5-cRib-YFP was still observed at week 8. Thus, successful delivery of the recombinant AAV vector and maintenance of the ribozyme expression and activity in the retina was confirmed even at week 8.

Example 13: Recombinant Viral Vector Optimization

Figure 17:
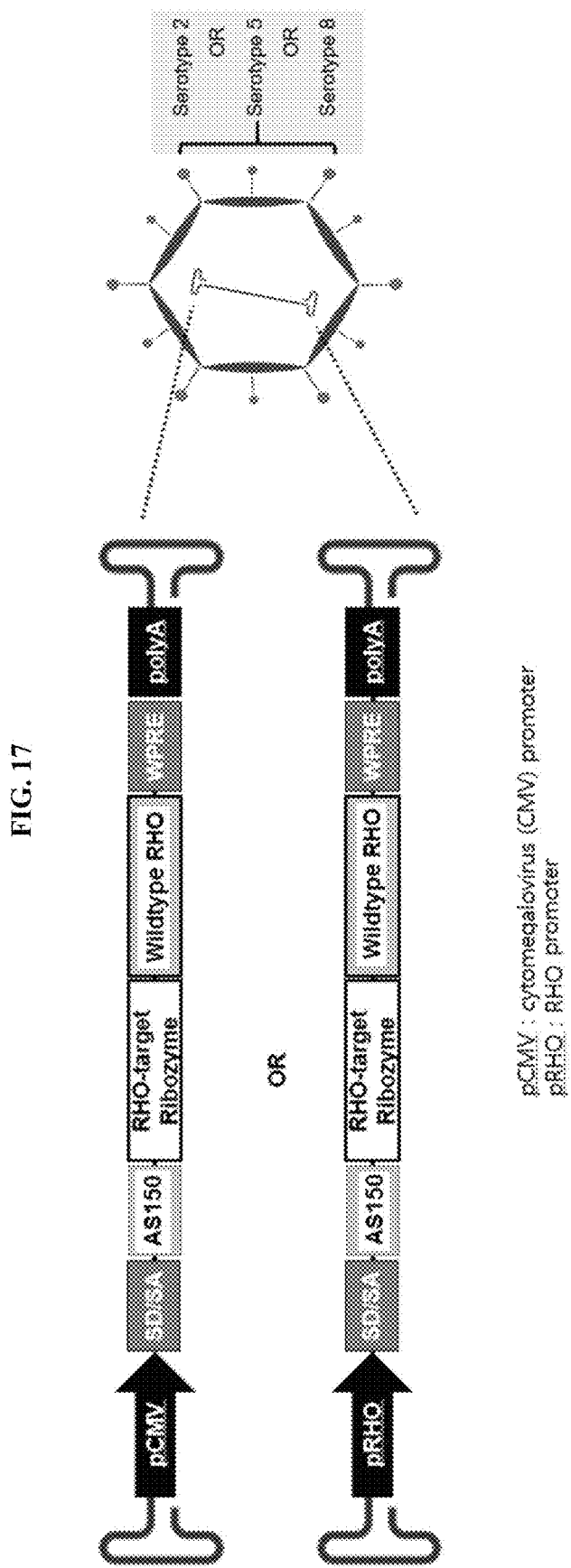
FIG. 17 is a schematic diagram of various recombinant AAV vectors containing RHO targeting ribozymes according to an embodiment of the present invention.

The ability of the various recombinant AAV vectors to infect and express in the retina was assessed (FIG. 17). As shown in FIG. 17, splicing donor/acceptor (SD/SA)

sequence is linked to ribozyme at the 5' end and WPRE (Woodchuck hepatitis virus Posttranscriptional Regulatory Element) is linked at the 3' end. SD/SA and WPRE sequences are represented by SEQ ID NO: 7 and SEQ ID NO: 9, respectively. Various recombinant AAV serotypes and different promoters were used to construct different recombinant viral vectors. For example, as promoters, CMV promoter and the RHO promoter were used. And, to evaluate efficacy of the final candidate, YFP sequence was removed, and to increase expression, WPRE was inserted.

13-1: Assessment of Ribozyme Distribution and Trans-Splicing Efficiency 3 weeks after administration of the prepared recombinant AAV vector in 5 weeks old hP23H-RFP mice, ribozyme distribution and trans-splicing were evaluated (FIG. 18).

The configurations of G1 to G7 are shown in FIG. 18 and in Table 2 below.

TABLE 2

| Group | Animal | Tested Substance | |
|---|---|---|---|
| G1 | P23H-RFP(+/−) | PBS | |
| G2 | | AAV2/5-cRib-YFP | AAV serotype 5, CMV Promoter |
| G3 | | AAV2/2 cRib-WPRE | AAV serotype 2, CMV Promoter |
| G4 | | AAV2/2 RL-Rib-WPRE | AAV serotype 2, RHO Promoter |
| G5 | | AAV2/5 cRib-WPRE | AAV serotype 5, CMV Promoter |
| G6 | | AAV2/5 RL-Rib-WPRE | AAV serotype 5, RHO Promoter |
| G7 | | AAV2/8 cRib-WPRE | AAV serotype 8, CMV Promoter |

Figure 18A:
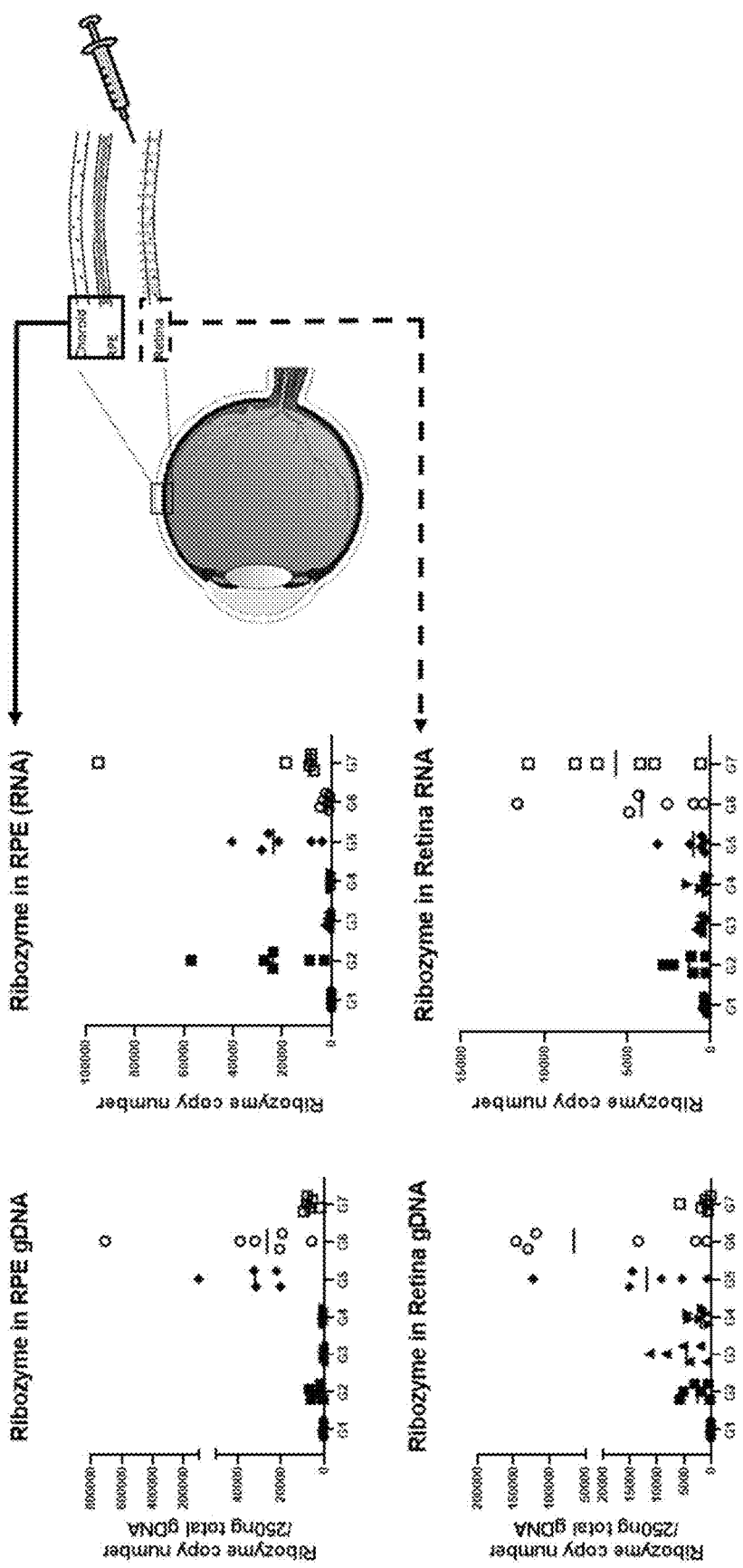
FIG. 18A and FIG. 18B show experimental result confirming the trans-splicing activity of RHO targeting ribozyme in a hP23H mouse-RFP ADRP mouse model at 3 weeks after administration of the recombinant AAV vector containing the ribozyme according to an embodiment of the present invention.

In order to check the infection rate for each serotype, the eyeballs of treated mice were removed 3 weeks after injection. Retina and RPE/choroid were separated and RNA and gDNA were extracted. When the extracted gDNA was compared, AAV serotype 5 showed more efficient transduction to both the retina and the RPE, than serotype 2 or 8. Parallel RNA analysis was performed by RT-PCR. The trans-splicing ribozyme was highly expressed in RPE as well under the CMV promoter regulation, while, in the retina, the ribozyme was highly expressed under the RHO promoter regulation compared to the ribozyme expression under the CMV promoter regulation (FIG. 18A).

Figure 18B:
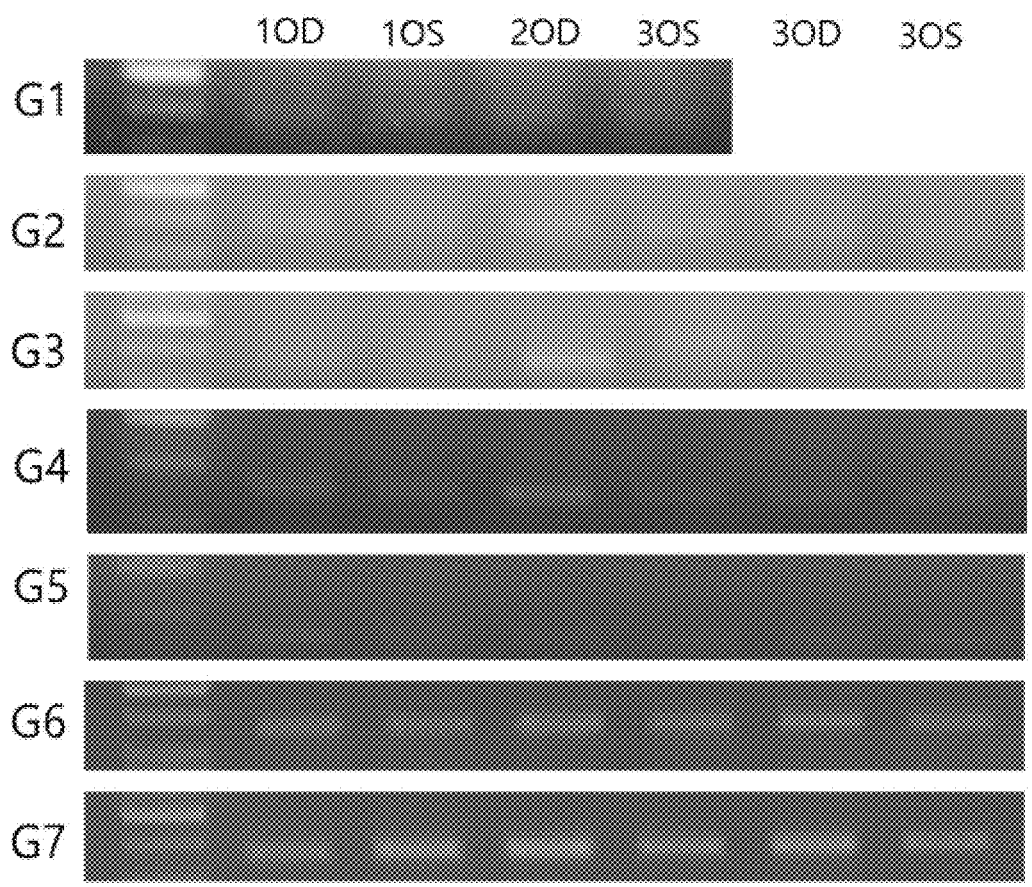

The presence of trans-splicing products through the trans-splicing action of the ribozyme in the retina was detected and confirmed by PCR. Then, the PCR bands of trans-splicing products formed by AAV serotype 5 under the RHO promoter regulation were dense (FIG. 18B).

The results indicate that AAV serotype 5 RL-Rib-WPRE showed excellent delivery and expression in the retina as well as excellent trans-splicing efficiency.

Figure 19:
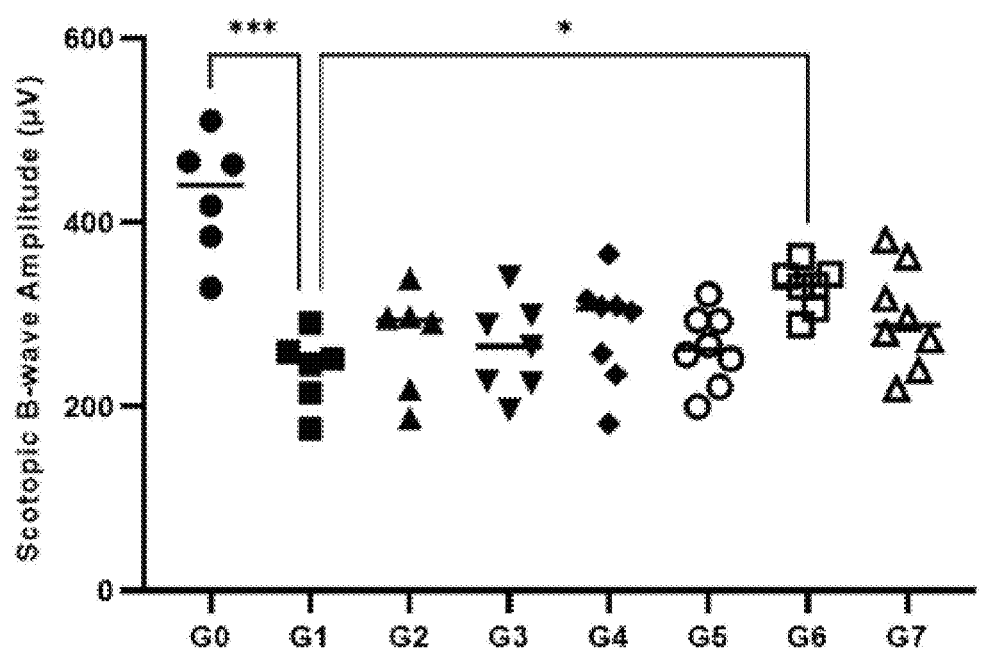
FIGS. 19 and 20 show electroretinograms of a hP23H mouse-RFP ADRP mouse model, after administration of a recombinant AAV vector containing the RHO targeting ribozyme according to an embodiment of the present invention.

13-2: Electroretinogram after Administration of Trans-Splicing Ribozyme in Mouse Model of RHO-adRP Electroretinogram examination was conducted at 6 weeks after administration of trans-splicing ribozyme in hP23H-RFP mice (5 weeks of age). The results are shown in FIG. 19 and Table 3.

TABLE 3

| Group | Animal | Tested Substance | B-wave (μV) |
|---|---|---|---|
| G0 | C57BL/6J (mRHO/mRHO) | PBS | 428.7 ± 65.15 |

TABLE 3-continued

| Group | Animal | Tested Substance | B-wave (μV) |
|---|---|---|---|
| G1 | P23H-RFP(+/−) | PBS | 240.1 ± 39.67 |
| G2 | | AAV2/5-cRib-YFP | 272.1 ± 56.75 |
| G3 | | AAV2/2 cRib-WPRE | 263.7 ± 40.46 |
| G4 | | AAV2/2 RL-Rib-WPRE | 284.9 ± 64.47 |
| G5 | | AAV2/5 cRib-WPRE | 263.4 ± 37.69 |
| G6 | | AAV2/5 RL-Rib-WPRE | 318.1 ± 26.35 |
| G7 | | AAV2/8-cRib-WPRE | 296.2 ± 57.86 |

B-wave amplitude of P23H-RFP mice (G1) was significantly decreased compared to the normal wild-type mice (G0). This result is consistent with the photoreceptor cells damage in P23H-RFP mice caused by the RHO mutation resulting impaired signal transmission.

When the electroretinogram was taken after administration of each AAV to the hP23H-RFP mice, it was confirmed that the average scotopic B-wave amplitude in all the test groups increased compared to the PBS-treated group (G1). Comparison between promoters showed that B-wave amplitude was significantly higher when RHO promoter was used than when CMV promoter was used (G3<G4, G5<G6), compared to the control group administered with PBS (G1). Comparison between serotypes, both AAV2/5 serotypes (G5, G6) and the AAV2/8 group (G7) showed significantly increased B-wave amplitude, compared to the PBS administration group (G1). The AAV2/5 RL-Rib-WPRE administration group exhibited the most significantly increased B-wave, indicating that subretinal administration of AAV2/5 RL-Rib-WPRE could show the highest effect of improving the visual function of the disease model.

Electroretinogram was performed at 4 weeks after administration of the following recombinant AAV vectors to 5 weeks-old hP23H-RFP mice: AAV2/5 RL-Rib-WPRE and AAV2/8 RL-Rib-WPRE, recombinant AAV vectors of serotype 5 and 8 with RHO promoter, respectively. The results in FIG. 20 and Table 4.

TABLE 4

| Group | Animal | Tested Substance | B-wave (μV) (0 week) | B-wave (μV) (4 week) |
|---|---|---|---|---|
| H1 | C57BL/6J (mRHO/mRHO) | PBS | 240.3 ± 52.45 | 267.8 ± 33.37 |
| H2 | P23H-RFP(+/−) | PBS | 173.7 ± 50.60 | 146.8 ± 41.18 |
| H3 | | AAV2/5 RL-Rib-WPRE | 176.1 ± 44.53 | 206.2 ± 33.59 |
| H4 | | AAV2/8 RL-Rib-WPRE | 191.5 ± 47.24 | 235.8 ± 36.06 |

Figure 20:
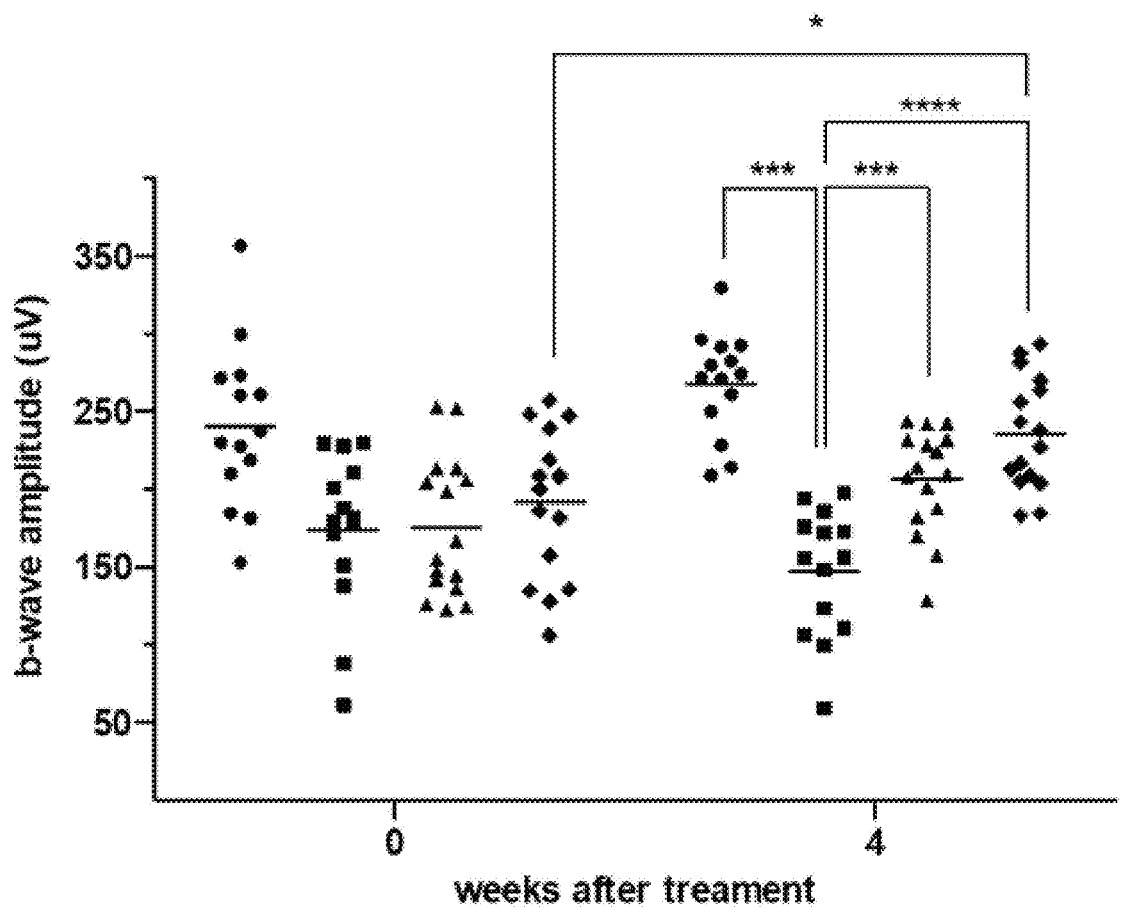

As shown in Table 4 and FIG. 20, the B-wave amplitude at 4 weeks after administration was significantly higher in AAV2/5 RL-Rib-WPRE (H3) group and AAV2/8 RL-Rib-WPRE group (H4), compared to PBS-treated group (H2). Considering that AAV2/8 RL-Rib-WPRE group (H4) showed higher B-wave before administration (0 week) than the PBS control group (H2) and the AAV2/5 RL-Rib-WPRE administration group (H3), we speculate that B-wave increasing ability of the AAV2/5 RL-Rib-WPRE administration group (H3) and the AAV2/8 RL-Rib-WPRE administration group (H4) were similar. Therefore, administration of AAV2/5 RL-Rib-WPRE and AAV2/8 RL-Rib-WPRE significantly improved visual function in this mouse model compared to the PBS-administered control group (H2).

Figure 21:
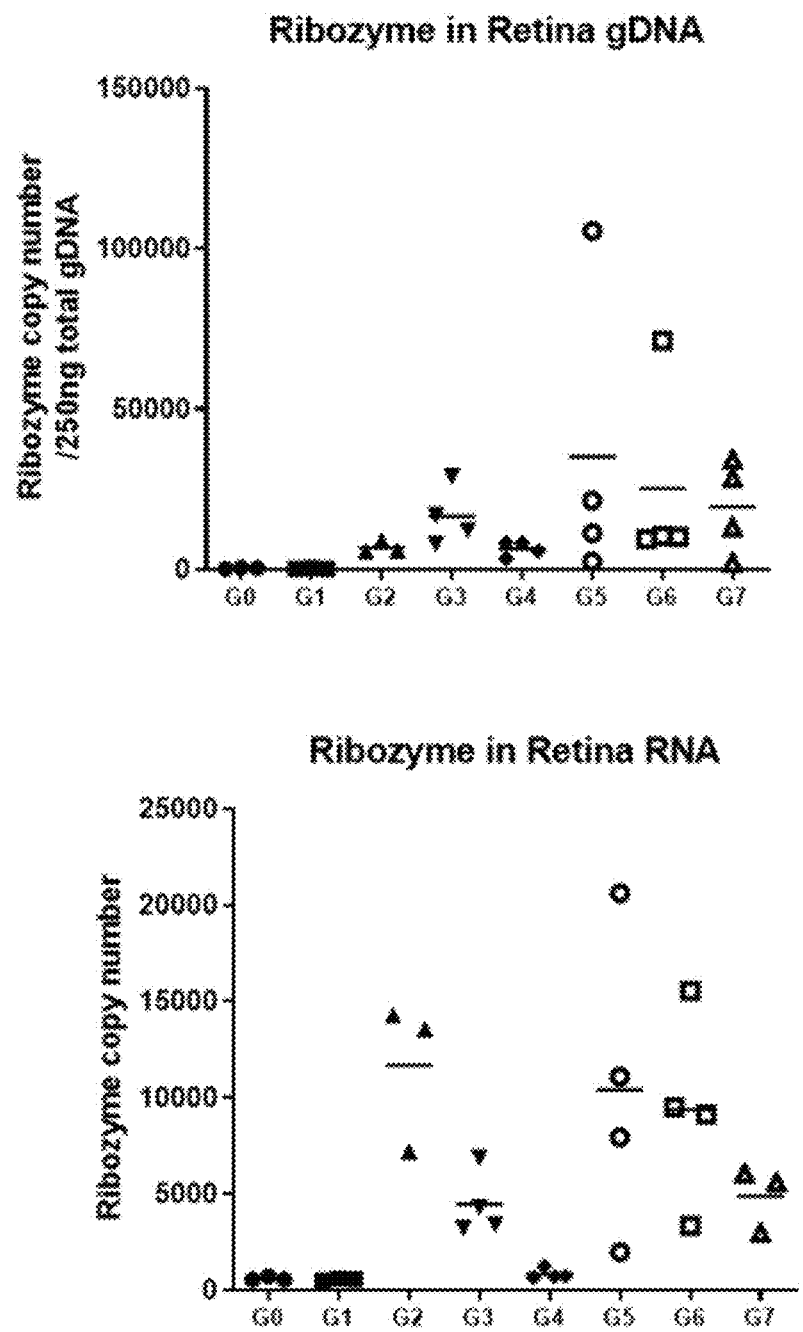
FIG. 21 shows ribozyme distribution and ribozyme RNA expression in the retina after administration of a recombinant AAV vector containing the RHO targeting ribozyme according to an embodiment of the present invention.

13-3: Distribution and Trans-Splicing Activity of Ribozyme in Retinal after Trans-Splicing Ribozyme Administration in Mouse Model of RHO-adRP The distribution of ribozyme in the retina and trans-splicing activity was assessed 6 weeks after administration of ribozyme to 5-week-old hP23H-RFP mice as shown in FIG. 21 and Table 5.

TABLE 5

| Group | Animal | Tested Substance |
|---|---|---|
| G0 | C57BL/6J (mRHO/mRHO) | PBS |
| G1 | P23H-RFP(+/−) | PBS |
| G2 |  | AAV2/5-cRib-YFP |
| G3 |  | AAV2/2 cRib-WPRE |
| G4 |  | AAV2/2 RL-Rib-WPRE |
| G5 |  | AAV2/5 cRib-WPRE |
| G6 |  | AAV2/5 RL-Rib-WPRE |
| G7 |  | AAV2/8-cRib-WPRE |

After confirming the functional efficacy in mouse model, the retinal gDNA and RNA was isolated and analyzed. AAV serotype 5 showed the same results as those seen at week 3 in Example 13-1 and it was confirmed that infection of the retina was successful. RNA analysis showed good ribozyme expression with AAV serotype 5 with RHO promoter. Delivery and expression of AAV2/5 RL-Rib-WPRE in the retina was stable at week 6.

Summarizing the above results, it was confirmed that AAV serotypes 5 and 8 was efficiently delivered into both retinal and RPE and the trans-splicing ribozyme regulated by RHO promoter was specifically expressed in the retina in the hP23H disease model.

Expression of trans-splicing ribozyme according to the present invention was maintained from week 3 of the initial administration to 6 weeks after administration, and improvement of visual function was observed as measured by electroretinography at weeks 4 and 6 after administration.

Aspects of the present invention has been described in detail above. Those of ordinary skill in the art would understand that these specific techniques are merely some of the preferred implementations. It is to be understood that the description above does not limit the scope of the present invention. The substantial scope of the present invention is defined by the claims and includes the equivalents.

What is claimed is:

1. A recombinant nucleic acid molecule comprising:
   (a) a trans-splicing ribozyme comprising a ribozyme sequence capable of splicing at a target splicing site of a target rhodopsin transcript with an internal guide sequence (IGS) complementarily binding to a binding region of the target rhodopsin transcript containing the target splicing site, wherein the binding region comprises 5 to 10 consecutive nucleotides; or
   (b) a recombinant DNA encoding the trans-splicing ribozyme of (a),
   wherein the IGS comprises a consecutive nucleotide sequence of 5-10 nt in length and is capable of complementarily binding and forming G/U wobble base pairs at the target splicing site of the target rhodopsin transcript, wherein the target splicing site comprises a nucleotide at the following positions: +30, +35, +42, +43, +52, +54, +55, +59, +75, +97, +116, +121, +123, +127, +132, +140, +154, +165, +171, +187, +191, +207, +215, +222, +230, +232, +235, +244, +256, +262, +273, +298, +308, +381, +403, +661 or +688, wherein the positions are identified with reference to SEQ ID NO: 1.

2. The recombinant nucleic acid molecule according to claim 1, wherein the trans-splicing ribozyme has a structure of 5'-IGS-ribozyme*-3', wherein the ribozyme* is a ribozyme sequence without an IGS.

3. The recombinant nucleic acid molecule according to claim 2, wherein the trans-splicing ribozyme further comprises an exon sequence at a position downstream of the ribozyme.

4. The recombinant nucleic acid molecule according to claim 1, wherein the target rhodopsin transcript comprises a mutation.

5. The recombinant nucleic acid molecule according to claim 4, wherein the mutation in the target rhodopsin transcript is mutation at one or more positions corresponding to position 1 to position 1142 of SEQ ID NO: 1.

6. The recombinant nucleic acid molecule according to claim 5, wherein the mutation is one or more selected from the group consisting of: L328P, T342M, Q344R/P/ter, V345L/M, A346P, P347A/R/Q/L/S/T, ter349/Q/E, N15S, T17M, V20G, P23A/H/L, Q28H, G51R/V, P53R, T58R/M, V87D/L, G89D, G106R/W, C110F/R/S/Y, E113K, L125R, W161R, A164E/V, C167R/W, P171Q/L/S, Y178N/D/C, E181K, G182S/V, C185R, C187G/Y, G188R/E, D190N/G/Y, H211R/P, C222R, P267R/L, S270R, K296N/E/M, R135G/L/P/W, T4K, T17M, M39R, N55K, G90V, M44T, V137M, G90D, T94I, A292E, A295V, F45L, V209M, F220C, P12R, R21C, Q28H, L40R, L46R, L47R, F52Y, F56Y, L57R, Y60ter, Q64ter, R69H, N78I, L79P, L88P, T92I, T97I, V104F, G109R, G114D/V, E122G, W126L/ter, S127F, L131P, Y136ter, C140S, T160T, M163T, A169P, P170H/R, S176F, P180A/S, Q184P, S186P/W, Y191C, T193M, M207R/K, V210F, I214N, P215L/T, M216R/L/K, R252P, T289P, S297R, A298D, K311E, N315ter, E341K, S343C, and Q312ter in the rhodopsin protein encoded by SEQ ID NO: 1.

7. The recombinant nucleic acid molecule according to claim 1, wherein the recombinant DNA encoding the trans-splicing ribozyme comprises the sequence of SEQ ID NO: 2, 3, or 4.

8. A non-viral gene carrier comprising nucleic acid molecule of claim 1.

9. The non-viral gene carrier according to claim 8, which is a lipid bilayer nanoparticle or liposome.

10. The recombinant nucleic acid molecule according to claim 3, wherein the exon sequence is a polynucleotide encoding a normal wild-type rhodopsin protein, a polynucleotide encoding a reporter protein, and/or a combination thereof.

11. The recombinant nucleic acid molecule according to claim 10, wherein the trans-splicing ribozyme of (a) further comprises an antisense sequence at a position upstream of the IGS, said antisense sequence being complimentary to a portion of the target rhodopsin transcript sequence.

12. A gene construct comprising the recombinant DNA of claim 1 and a promoter sequence operably linked the recombinant DNA to express the trans-splicing ribozyme.

13. A gene construct comprising the recombinant DNA of claim 3 and a promoter sequence operably linked the recombinant DNA to express the trans-splicing ribozyme.

14. A recombinant expression vector comprising the gene construct according to claim 12.

15. A recombinant virus comprising the gene construct according to claim 13.

16. A non-viral gene carrier comprising the recombinant nucleic acid molecule of claim 10.

17. The recombinant virus of claim 15, wherein the virus is selected from the group consisting of adenovirus, adeno-associated virus (AAV), retrovirus, lentivirus, herpes simplex virus, and vaccinia virus.

18. The recombinant virus of claim 15, wherein the virus is a recombinant adeno-associated virus (AAV) comprising a polynucleotide encoding the trans-splicing ribozyme, wherein the polynucleotide is operably linked to a promoter sequence; and wherein the recombinant AAV is derived from a native or artificial adenovirus serotype, an isolate thereof, or a clade thereof.

19. A pharmaceutical composition comprising any of the following (i)-(vii):

(i) the recombinant nucleic acid molecule according to claim 1;

(ii) a non-viral gene carrier comprising nucleic acid molecule of claim 1;

(iii) a gene construct comprising the recombinant DNA of claim 1 and a promoter sequence operably linked the recombinant DNA to express the trans-splicing ribozyme;

(iv) a recombinant expression vector comprising the gene construct (iii);

(v) a recombinant virus comprising the gene construct (iii) or the recombinant expression vector (iv);

(vi) a non-viral gene carrier comprising the gene construct (iii) or the recombinant expression vector (iv);

(vii) a combination of one or more of (i)-(vi), as an active ingredient, and a pharmaceutically acceptable carrier.

20. The pharmaceutical composition of claim 19, wherein the trans-splicing ribozyme further comprises an exon sequence at a position downstream of the ribozyme.

21. The pharmaceutical composition of claim 19, wherein the target rhodopsin transcript comprises a mutation.

22. A method of treatment or prevention of retinitis pigmentosa in a subject in need thereof, comprising administering the pharmaceutical composition of claim 19 to the subject.

* * * * *